US008343743B2

(12) United States Patent
Oyler et al.

(10) Patent No.: US 8,343,743 B2
(45) Date of Patent: *Jan. 1, 2013

(54) DESIGNER UBIQUITIN LIGASES HAVING A NON-CLEAVABLE SNAP25 DOMAIN AND E3-LIGASE DOMAIN

(75) Inventors: George A. Oyler, Baltimore, MD (US); Yien Che Tsai, Frederick, MD (US)

(73) Assignee: Synaptic Research, LLC, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/482,420

(22) Filed: Jun. 10, 2009

(65) Prior Publication Data

US 2010/0015116 A1    Jan. 21, 2010

Related U.S. Application Data

(60) Provisional application No. 61/060,324, filed on Jun. 10, 2008.

(51) Int. Cl.
*C12N 9/00* (2006.01)
*C12N 1/20* (2006.01)
*C12N 15/00* (2006.01)
*C07H 21/04* (2006.01)
*A61K 38/43* (2006.01)

(52) U.S. Cl. .................... 435/183; 424/94.1; 435/252.3; 435/320.1; 536/23.2

(58) Field of Classification Search .................... None
See application file for complete search history.

(56) References Cited

U.S. PATENT DOCUMENTS
2006/0153876 A1    7/2006 Sanders

FOREIGN PATENT DOCUMENTS
WO    WO 01/58936    8/2001
WO    WO 2004/076634    9/2004

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Kuo, C. L. et al., "Accelerated Neuronal Cell Recovery from *Botulinum* Neurotoxin Intoxication by Targeted Ubiquitination," *PLoS One*, 6:(5):1-10 (2011).
Zhou, P., et al., "Harnessing the Ubiquitination Machinery to Target the Degradation of Specific Cellular Proteins," *Molecular Cell*, 6: 751-756 (2000).
Kuo, C. L., et al., "Lipid and cationic polymer based transduction of botulinum holotoxin, or toxin protease alone, extends the target cell range and improves the efficiency of intoxication," *Toxicon*, 55 (2-3): 619-629 (2010).
Gutierrez, L. M., et al., "A Peptide That Mimics the C-terminal Sequence of SNAP-25 Inhibits Secretory Vesicle Docking in Chromaffin Cells," *J. Biol. Chem.*, 272(5):2634-2639 (1997).

Xia, Z., et al., "TRAF2: A Double-Edge Sword?," *Science's STKE*, 1-4 (2005).
Cardozo, T., et al., "The SCF Ubiquitin Ligase: Insights Into a Molecular Machine," *Nature Reviews: Molecular Cell Biology*, 5:739-751 (2004).
Simpson, Lance. L., "Identification of the characteristics that underlie botulinum toxin potency: implications for designing novel drugs," *Biochimie*, 82:943-953 (2000).
Jahn, R., et al., "Molecular Mechanisms of Clostridial Neurotoxins," *Annals New York Academy of Sciences*, 733:245-255 (1994).
Eleopra, R., et al., "Different time courses of recovery after poisoning with botulinum neurotoxin serotypes A and E in humans," *Neuroscience Letters*, 256:135-138 (1998).
Binz, T., et al., "Proteolysis of SNAP-25 by Types E and A Botulinal Neurotoxins," *The Journal of Biological Chemistry*, 269(3):1617-1620 (1994).
Ferrer-Montiel, A., et al., "The 26-mer peptide released from SNAP-25 cleavage by botulinum neurotoxin E inhibits vesicle docking," *FEBS Letters*, 435:84-88 (1998).
Raciborska, D., et al., "Retention of Cleaved Synaptosome-Associated Protein of 25 kDa (SNAP-25) in Neuromuscular Junctions: A New Hypothesis to Explain Persistence of Botulinum A Poisoning," *Can. J. Physiol. Pharmacol.*, 77:679-688 (1999).
Keller, J., et al., "Persistence of botulinum neurotoxin action in cultured spinal cord cells [1,2]," *FEBS Letters*, 456:137-142 (1999).
Adler, M., et al., "Persistence of botulinum neurotoxin A demonstrated by sequential administration of serotypes A and E in rat EDL Muscle," *Toxicon*, 39:233-243(2001).
Fernández-Salas, E., et al., "Plasma membrane localization signals in the light chain of botulinum neurotoxin" *PNAS*, 101(9):3208-3213 (2004).
Deshaies, R., et al., "RING Domain E3 Ubiquitin Ligases," *Annu. Rev. of Biochem.*, 78:399-434 (2009).
Varshavsky, A., "The N-end Rule: Functions, Mysteries, Uses," *Proc. Natl. Acad. Sci. USA* 93:12142-12149 (1996).
Ivanov, V., et al., "Expression of Ring Finger-Deleted TRAF2 Sensitizes Metastatic Melanoma Cells to Apoptosis Via Up-Regulation of p38, TNFα and Suppression of NF-κB Activities," *Oncogene* 20:2243-2253 (2001).
O'Sullivan, G., et al., "Rescue of Exocytosis in Botulinum Toxin A-Poisoned Chromaffin Cells by Expression of Cleavage-Resistant SNAP-25. Identification of the Minimal Essential C-Terminal Residues," *The Journal of Biological Chemistry*, 274(52):36897-36904 (1999).
Washbourne, P., et al., "Botulinum Neurotoxin E-Insensitive Mutants of SNAP-25 Fail to Bind VAMP but Support Exocytosis," *Journal of Neurochemistry*, 73:2424-2433 (1999).

(Continued)

*Primary Examiner* — Christian Fronda
(74) *Attorney, Agent, or Firm* — Antoinette G. Giugliano, PC; AGG Intellectual Property Law

(57) ABSTRACT

The present invention relates to a designer or recombinant ubiquitin ligase molecule that includes a toxin binding domain that is specific for a toxin active fragment, wherein the toxin active fragment is an enzymatically active fragment of one or more toxins or toxin serotypes; and an E3-ligase domain that comprises an E3-ligase or polypeptide that facilitates E2-mediated ubiquitination of the toxin active fragment. In an embodiment, the composition further includes a delivery system that allow the designer ubiquitin ligase to enter the cell. The present invention further includes methods for treating an individual intoxicated with a toxin by administering the designer ubiquitin ligase of the present invention.

24 Claims, 11 Drawing Sheets

OTHER PUBLICATIONS

Fernández-Salas, E., et al., "Is the Light Chain Subcelluar Localiza Scheffner, M., et al., "The HPV-16 E6 and E6-AP Complex Functions as a Ubiquitin-Protein Ligase in the Ubiquitination of p53," *Cell*, 75:495-505 (1993).

Lorick, K., et al., "RING Fingers Mediate Ubiquitin-Conjugating Enzyme (E2)-Dependent Ubiquitination," *Proc. Natl. Acad. Sci. USA*, 96:11364-11369 (1999).

Foran, P., et al., "Evaluation of the Therapeutic Usefulness of Botulinum Neurotoxin B, C1, E, and F Compared with the Long Lasting Type A. Basis for Distinct Durations of Inhibition of Exocytosis in Central Neurons," *The Journal of Biological Chemistry* 278:1363-1371 (2003). tion an Important Factor in Botulinum Toxin Duration of Action?," *Movement Disorders*, 19(Suppl. 8):S23-S34 (2004).

Alvarez, S., et al., "Sphingosine-1-Phosphate is a Missing Cofactor for the E3 Ubiquitin Ligase TRAF2," *Nature*, 465:1084-1088 (2010).

Sakamoto K., et al., "Development of Protacs to Target Cancer-Promoting Proteins for Ubiquitination and Degradation," *Molecular and Cellular Proteomics* 2:1350-1358 (2003).

Rodriguez-Gonzalez A., et al., "Targeting Steroid Hormone Receptors for Ubiquitination and Degradation in Breast and Prostate Cancer," *Oncogene*, 27:7201-7211 (2008).

Sakamoto, K., et al., "Protacs: Chimeric Molecules that Target Proteins to the Skp1-Cullin-F Box Complex for Ubiquitination and Degradation," *Proc. Natl. Acad. Sci. USA*, 98: 8554-8559 (2001).

Lalli, G., et al., "Functional Characterisation of Tetanus and Botulinum Neurotoxins Binding Domains," *Journal of Cell Science*, 112(Pt 16): 2715-2724 (1999).

Lacy, B., et al., "Crystal Structure of Botulinum Neurotoxin Type A and Implications for Toxicity," *Nature Structural Biology*, 5: 898-902 (1998).

Blasi, J., et al., "Botulinum Neurotoxin A Selectively Cleaves the Synaptic Protein SNAP-25," *Nature*, 365: 160-163 (1993).

Schiavo, G., et al., "Tetanus and Botulinum-B Neurotoxins Block Neurotransmitter Release by Proteolytic Cleavage of Synaptobrevin," *Nature*, 359: 832-835 (1992).

Schiavo, G., et al., "Identification of the Nerve Terminal Targets of Botulinum Neurotoxin Serotypes A, D, and E," *J. Biol. Chem.*, 268(32): 23784-23787(1993).

Schiavo, G., et al., "Botulinum Neurotoxins Serotypes A and E Cleave SNAP-25 at Distinct COOH-Terminal Peptide Bonds," *FEBS Letters*, 335(1): 99-103 (1993).

Kozaki, S., et al., "Immunological Characterization of Papain-Induced Fragments of Clostridium Botulinum Type A Neurotoxin and Interaction of the Fragments with Brain Synaptosomes," *Infection and Immunity*, 57: 2634-2639 (1989).

Montecucco, C., et al., "Botulinal Neurotoxins: Revival of an Old Killer," *Current Opinion in Pharmacology*, 5: 274-279 (2005).

Tsai, Y. C., et al., "Targeting Botulinum Neurotoxin Persistence by the Ubiquitin-Proteasome System," *PNAS*, 107(38): 16554-16559 (2010).

Westbrook, T., et al., "SCF$^{\beta TRCP}$ Controls Oncogenic Transformation and Neural Differentiation Through REST Degradation," *Nature*, 452: 370-374 (2008).

Kipreos, E., et al., "The F-box Protein Family," *Genome Biol.*, 1:3002.1 (2000).

Bai, C., et al., "SKP1 Connects Cell Cycle Regulators to the Ubiquitin Proteolysis Machinery Through a Novel Motif, the F-Box," *Cell*, 86: 263-274 (1996).

Arbabi, G. M., et al., "Selection and Identification of Single Domain Antibody Fragments From Camel Heavy-Chain Antibodies," *FEBS Letters*, 414: 521-526 (1997).

Gibbs, W., "Nanobodies," *Scientific American*, 293: 78-83 (2005).

van der Linden, R.H.J., et al., "Comparison of Physical Chemical Properties of Llama VHH Antibody Fragments and Mouse Monoclonal Antibodies," *Biochim. Biophys. Acta.*, 1431(5): 37-46 (1999).

Dumoulin, M., et al., "Single-Domain Antibody Fragments With High Conformational Stability," *Protein Science*, 11: 500-515 (2002).

Lauwereys, M., et al., "Potent Enzyme Inhibitors Derived From Dromedary Heavy-Chain Antibodies," *Embo Journal*, 17(13): 3512-3520 (1998).

Tremblay, J.M., et al., "Camelid Single Domain Antibodies (VHHs) as Neuronal Cell Intrabody Binding Agents and Inhibitors of *Clostridium botulinum* Neurotoxin (BoNT) Proteases," *Toxicon*, 56: 990-998 (2010).

Lassot, I., et al., "ATF4 Degradation Relies on a Phosphorylation-Dependent Interaction With the SCF(betaTrCP) Ubiquitin Ligase," *Mol. Cell. Biol.*, 21: 2192-2202 (2001).

Sakamoto, K.M., "Chimeric Molecules to Target Proteins for Ubiquitination and Degradation," *Methods in Enzymology*, 399: 833-847 (2005).

Wesolowski, J., et al., "Single Domain Antibodies: Promising Experimental and Therapeutic Tools in Infection and Immunity," *Med. Microbiol. Immunol.* 198: 157-174 (2009).

Dong, J., et al., "A Single-Domain Llama Antibody Potently Inhibits the Enzymatic Activity of Botulinum Neurotoxin by Binding to the Non-Catalytic Alpha-Exosite Binding Region," *J. Mol. Biol.*, 397(4): 1106-1118 (2010).

Zhang, P., et al., "An Efficient Drug Delivery Vehicle for Botulism Countermeasure," *BMC Pharmacology*, 9: 12 (2009).

Ho, M., et al., "Recombinant Botulinum Neurotoxin A Heavy Chain-Based Delivery Vehicles for Neuronal Cell Targeting," *Protein Eng. Des. Sel.*, 24(3): 247-253 (2011).

Yang, G., et al., "Expression of Recombinant *Clostridium difficile* Toxin A and B in *Bacillus megaterium*," *BMC Microbiology*, 8: 192 (2008).

Sun, X., et al., "Essential Role of the Glucosyltransferase Activity in *Clostridium difficile* Toxin-Induced Secretion of TNF-α by Macrophages," *Microb. Pathog.*, 46(6): 298-305(2009).

Fahrer, J., et al., "Genetically Engineered Clostridial C2 Toxin as a Novel Delivery System for Living Mammalian Cells," *Bioconjugate Chem.*, 21: 130-139 (2010).

Keefe, A.D., et al., "One-Step Purification of Recombinant Proteins Using a Nanomolar-Affinity Streptavidin-Binding Peptide, the SBP-Tag," *Protein Expression and Purification*, 23: 440-446 (2001).

The website downloaded on Jul. 17, 2011 from ebi.ac.uk/interpro/potm/2004_12/Page2.htm.

Wells, J., "Additivity of Mutational Effects in Proteins," *Biochemistry*, 29(37):8509-8517 (1990).

Ngo, T., et al., "Computational Complexity, Protein Structure Prediction, and the Levinthal Paradox," *The Protein Problem and Tertiary Structure Prediction*, pp. 492-495 (1994).

Bork, P., "Powers and Pitfalls in Sequence Analysis: The 70% Hurdule," *Genome Research*, 10:398-400 (2000).

Skolnick, J., et al., "From genes to Protein Structure and Function: Novel Applications of Computational Approaches in the Genomic Era," *Trend in Biotech.*, 18:34-39 (2000).

Doerks, T., "Protein Annotation: Detective Work for Function Prediction," *Trends in Genetics*, 14:248-250 (1998).

Smith, T., et al., "The Challenges of genome Sequence Annotation or "The Devil is in the Details"," *Nature Biotechnology*, 15:1222-1223 (1997).

Brenner, S., "Errors in Genome Annotation," *Trends in Genetics*, 15(4):132-133 (1999).

Bork, P., "Go Hunting in Sequance Databases but Watch Out for the Traps," *Trends in Genetics*, 12(10):425-1427 (1996).

Oyler, G., et al., "Therapeutics which Accelerate Degradation BoNT/ALC within Neurons," *Toxicon*, 51:1-54 (2008).

Habermann, E., et al., "Clostridial Neurotoxins: Handling and Action at the Cellular and Molecular Level," *Curr. Top. Microbiol. Immunol.*, 129:93-179 (1986).

Montecucco, C., et al., "Structure and Function of Tetanus and Botulinum Neurotoxins," *Q. Rev. Biophys.* 28(4):423-472 (1995).

Chen, Z. J., "Ubiquitin Signaling in the NF-kappaB Pathway," *Nat. Cell. Biol.*, 7(8):758-765 (2005.

Blasi, J., et al., "Botulinum Neurotoxin C1 Blocks Neurotransmitter Release by Means of Cleaving HPC-1/Syntaxin," *EMBO J.*, 12(12): 4821-4828 (1993).

Schiavo, G., et al., "Botulinum G Neurotoxin Cleaves VAMP/Synaptobrevin at a Single Ala-Ala Peptide Bond," *J. Biol. Chem.*, 269(32): 20213-20216 (1994).

Deshaies, R. J., "SCF and Cullin/Ring H2-Based Ubiquitin Ligases," *Annu. Rev. Cell. Dev. Biol.*, 15: 435-467 (1999).

Davis, M., et al., "Pseudosubstrate Regulation of the SCF(beta-TrCP) Ubiquitin Ligase by hnRNP-U," *Genes. Dev.*, 16: 439-451 (2002).

de Paiva, Anton et al., "Light chain of botulinum nuerotoxin is active in mammalian motor nerve terminals when delivered via liposomes." *Febs Letters*, Elsevier, 277(1-2); 171-174 (1990).

Webb, R. P., et al., "Production of Catalytically Inactive BoNT/A1 Holoprotein and Comparison with BoNT/A1 Subunit Vaccines Against Toxin Subtypes A1, A2, and A3," *Vaccine*, 27(33): 4490-4497 (2009). (From PubMed, Abstract No. 19450643).

Oyler, F., et al., "The role of ubiquitin and ubiquitin-like molecules in neuronal persistence of botulinum neurotoxin," Paper presented at the SALK-sponsored Workshop, Ubiquitin and Ubiquitin-like Modifications in Viral Infection and Immunity, NIH Natcher Conference Center, Bethesda, MD (Aug. 2007).

Schiavo, G., et al., "Botulinum Neurotoxin Serotype F is a Zinc Endopeptidase Specific for VAMP/Synaptobrevin," *J. Biol. Chem.*, 268(16): 11516-11519 (1993). (From PubMed, Abstract No. 8505288).

Van Bockstaele, F., et al., "The Development of Nanobodies for Therapeutic Applications," *Curr. Opin. Investig. Drugs*, 10(11): 1212-1224 (2009). (From PubMed, Abstract No. 19876789).

* cited by examiner

Fig. 2

Identify an effective E3-ligase or E3-ligase targeting domain

Non-cleavable SNAP25 (SNAP25/NC) was used as the targeting domains.

Seven different E3-ligase or E3-ligase binding domains were selected for testing, each expressed as a YFP fusion.

1. YFP/ SNAP25/NC /RING
2. YFP/ SNAP25/NC /HECT
3. YFP/ SNAP25/NC /IkB
4. YFP/ SNAP25/NC /HIF
5. YFP/ SNAP25/NC /U-box
6. YFP/ SNAP25/NC /RIBRR
7. YFP/ SNAP25/NC /βrCP

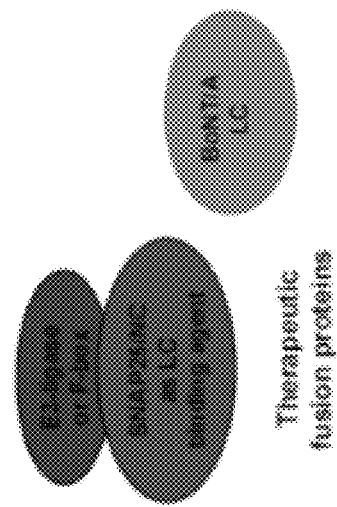

"Designer E3 ligase"

Therapeutic fusion proteins

Immunoprecipitation followed by western to assess ubiquitin modification

SNAP-25/NC control
SNAP-25/NC-RING

Ubi$_n$ YFP-BoNT/A LC anti-Ubi

SNAP-25/NC control
SNAP-25/NC-RING anti-GFP

YFP-BoNT/A LC ▶

Fig. 6B

Western blot to assess steady state levels of transfected YFP-BoNT/A LC modification SNAP-25/NC control
SNAP-25/NC-RING

— 75 KD anti-GFP

YFP- LCA

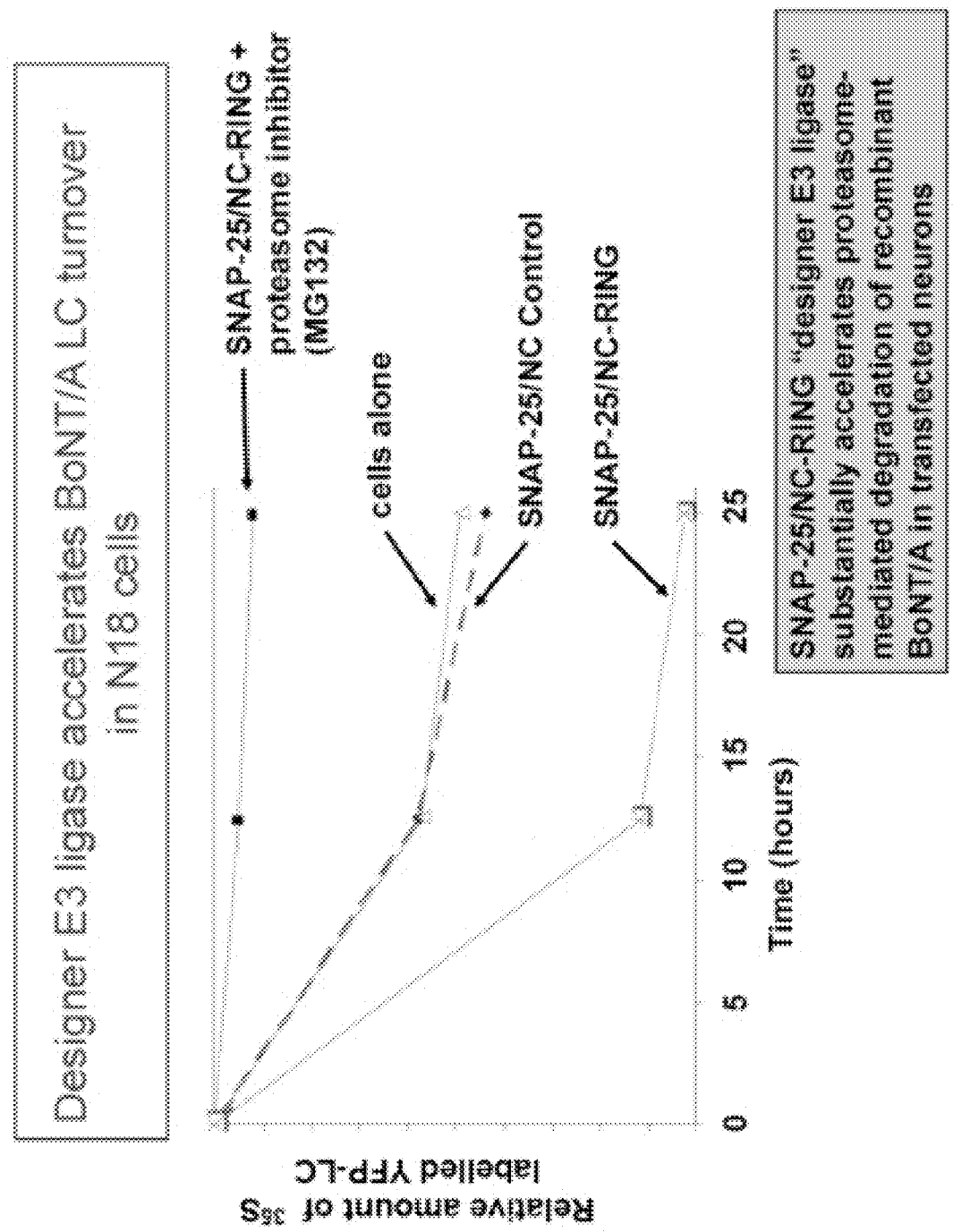

SNAP25A

ATGGCTGAAGATGCTGATATGCGTAATGAACTTGAAGAAATGCAACGTCGTGCTGATCAA
CTTGCTGATGAATCTCTTGAATCTACTCGTCGTATGCTTCAACTTGTTGAAGAATCTAAA
GATGCTGGTATTCGTACTCTTGTTATGCTTGATGAACAAGGTGAACAACTTGATCGTGTT
GAAGAAGGTATGAATCATATTAATCAAGATATGAAAGAAGCTGAAAAAAATCTTAAAGAT
CTTGGTAAATGTTGTGGTCTTTTTATTTGTCCTTGTAATAAACTTAAATCTTCTGATGCT
TATAAAAAAGCTTGGGGTAATAATCAAGATGGTGTTGTTGCTTCTCAACCTGCTCGTGTT
GTTGATGAACGTGAACAAATGGCTATTTCTGGTGGTTTTATTCGTCGTGTTACTAATGAT
GCTCGTGAAAATGAAATGGATGAAAATCTTGAACAAGTTTCTGGTATTATTGGTAATCTT
CGTCATATGGCTCTTGATATGGGTAATGAAATTGATACTCAAAATCGTCAAATTGATCGT
ATTATGGAAAAAGCTGATTCTAATAAAACTCGTATTGATGAAGCTAATCAACGTGCTACT
AAAATGCTTGGTTCTGGT (SEQ ID NO: 1)

1 maedadmrne leemqrradq ladeslestr rmlqlveesk dagirtlvml deqgeqldrv
   61 eegmnhinqd mkeaeknlkd lgkccglfic pcnklkssda ykkawgnnqd gvvasqparv
  121 vdereqmais ggfirrvtnd arenemdenl eqvsgiignl rhmaldmgne idtqnrqidr
  181 imekadsnkt rideanqrat kmlgsg (SEQ ID NO: 2)

SNAP25B

ATGGCTGAAGATGCTGATATGCGTAATGAACTTGAAGAAATGCAACGTCGTGCTGATCAA
CTTGCTGATGAATCTCTTGAATCTACTCGTCGTATGCTTCAACTTGTTGAAGAATCTAAA
GATGCTGGTATTCGTACTCTTGTTATGCTTGATGAACAAGGTGAACAACTTGAACGTATT
GAAGAAGGTATGGATCAAATTAATAAAGATATGAAAGAAGCTGAAAAAAATCTTACTGAT
CTTGGTAAATTTTGTGGTCTTTGTGTTTGTCCTTGTAATAAACTTAAATCTTCTGATGCT
TATAAAAAAGCTTGGGGTAATAATCAAGATGGTGTTGTTGCTTCTCAACCTGCTCGTGTT
GTTGATGAACGTGAACAAATGGCTATTTCTGGTGGTTTTATTCGTCGTGTTACTAATGAT
GCTCGTGAAAATGAAATGGATGAAAATCTTGAACAAGTTTCTGGTATTATTGGTAATCTT
CGTCATATGGCTCTTGATATGGGTAATGAAATTGATACTCAAAATCGTCAAATTGATCGT
ATTATGGAAAAAGCTGATTCTAATAAAACTCGTATTGATGAAGCTAATCAACGTGCTACT
AAAATGCTTGGTTCTGGT (SEQ ID NO: 3)

1 maedadmrne leemqrradq ladeslestr rmlqlveesk dagirtlvml deqgeqleri
   61 eegmdqinkd mkeaeknltd lgkfcglcvc pcnklkssda ykkawgnnqd gvvasqparv
  121 vdereqmais ggfirrvtnd arenemdenl eqvsgiignl rhmaldmgne idtqnrqidr
  181 imekadsnkt rideanqrat kmlgsg (SEQ ID NO: 4)

Two mutations to make either SNAP25A or SNAP25B uncleavable D179K and R198T

GGTAATCTTCGTCATATGGCTCTTGATATGGGTAATGAAATTGATACTCAAAATCGTCAA
ATTAAACGTATTATGGAAAAAGCTGATTCTAATAAAACTCGTATTGATGAAGCTAATCAA
ACTGCTACTAAAATGCTTGGTTCTGGT (SEQ ID NO: 5)

GNLRHMALDMGNEIDTQNRQIKRIMEKADSNKTRIDEANQTATKMLGSG (SEQ ID NO: 6)

FIG. 8A

Full length XIAP

```
497 aa              linear
DEFINITION    RecName: Full=Baculoviral IAP repeat-containing protein 4; AltName:
              Full=E3 ubiquitin-protein ligase XIAP ATGACTTTTAATTCTTTTGAAGGTTCTAAAACTTGTGTTCCTGCTGATATTAATAAAGAA
GAAGAATTTGTTGAAGAATTTAATCGTCTTAAAACTTTTGCTAATTTTCCTTCTGGTTCT
CCTGTTTCTGCTTCTACTCTTGCTCGTGCTGGTTTTCTTTATACTGGTGAAGGTGATACT
GTTCGTTGTTTTCTTGTCATGCTGCTGTTGATCGTTGGCAATATGGTGATTCTGCTGTT
GGTCGTCATCGTAAAGTTTCTCCTAATTGTCGTTTTATTAATGGTTTTTATCTTGAAAAT
TCTGCTACTCAATCTACTAATTCTGGTATTCAAAATGGTCAATATAAAGTTGAAAATTAT
CTTGGTTCTCGTGATCATTTTGCTCTTGATCGTCCTTCTGAAACTCATGCTGATTATCTT
CTTCGTACTGGTCAAGTTGTTGATATTTCTGATACTATTTATCCTCGTAATCCTGCTATG
TATTCTGAAGAAGCTCGTCTTAAATCTTTTCAAAATTGGCCTGATTATGCTCATCTTACT
CCTCGTGAACTTGCTTCTGCTGGTCTTTATTATACTGGTATTGGTGATCAAGTTCAATGT
TTTTGTTGTGGTGGTAAACTTAAAAATTGGGAACCTTGTGATCGTGCTTGGTCTGAACAT
CGTCGTCATTTTCCTAATTGTTTTTTTGTTCTTGGTCGTAATCTTAATATTCGTTCTGAA
TCTGATGCTGTTTCTTCTGATCGTAATTTTCCTAATTCTACTAATCTTCCTCGTAATCCT
TCTATGGCTGATTATGAAGCTCGTATTTTTACTTTTGGTACTTGGATTTATTCTGTTAAT
AAAGAACAACTTGCTCGTGCTGGTTTTTATGCTCTTGGTGAAGGTGATAAAGTTAAATGT
TTTCATTGTGGTGGTGGTCTTACTGATTGGAAACCTTCTGAAGATCCTTGGGAACAACAT
GCTAAATGGTATCCTGGTTGTAAATATCTTCTTGAACAAAAAGGTCAAGAATATATTAAT
AATATTCATCTTACTCATTCTCTTGAAGAATGTCTTGTTCGTACTACTGAAAAAACTCCT
TCTCTTACTCGTCGTATTGATGATACTATTTTTCAAAATCCTATGGTTCAAGAAGCTATT
CGTATGGGTTTTTCTTTTAAAGATATTAAAAAAATTATGGAAGAAAAAATTCAAATTTCT
GGTTCTAATTATAAATCTCTTGAAGTTCTTGTTGCTGATCTTGTTAATGCTCAAAAAGAT
TCTATGCAAGATGAATCTTCTCAAACTTCTCTTCAAAAAGAAATTTCTACTGAAGAACAA
CTTCGTCGTCTTCAAGAAGAAAAACTTTGTAAAATTTGTATGGATCGTAATATTGCTATT
GTTTTTGTTCCTTGTGGTCATCTTGTTACTTGTAAACAATGTGCTGAAGCTGTTGATAAA
TGTCCTATGTGTTATACTGTTATTACTTTTAAACAAAAAATTTTTATGTCT (SEQ ID NO: 7)

ORIGIN
    1 mtfnsfegsk tcvpadinke eefveefnrl ktfanfpsgs pvsastlara gflytgegdt
   61 vrcfschaav drwqygdsav grhrkvspnc rfingfylen satqstnsgi qngqykveny
  121 lgsrdhfald rpsethadyl lrtgqvvdis dtiyprnpam yseearlksf qnwpdyahlt
  181 prelasagly ytgigdqvqc fccggklknw epcdrawseh rrhfpncffv lgrnlnirse
  241 sdavssdrnf pnstnlprnp smadyearif tfgtwiysvn keqlaragfy algegdkvkc
  301 fhcgggltdw kpsedpweqh akwypgckyl leqkgqeyin nihlthslee clvrttektp
  361 sltrriddti fqnpmvqeai rmgfsfkdik kimeekiqis gsnykslevl vadlvnaqkd
  421 smqdessqts lqkeisteeq lrrlqeeklc kicmdrniai vfvpcghlvt ckqcaeavdk
  481 cpmcytvitf kqkifms     (SEQ ID NO: 8)
```

FIG. 8B

XIAP domain containing the RING domain that was used to make the designer ligase with non-cleavable SNAP25

```
TCTCTTACTCGTCGTATTGATGATACTATTTTTCAAAATCCTATGGTTCAAGAAGCTATT
CGTATGGGTTTTTCTTTTAAAGATATTAAAAAAATTATGGAAGAAAAAATTCAAATTTCT
GGTTCTAATTATAAATCTCTTGAAGTTCTTGTTGCTGATCTTGTTAATGCTCAAAAAGAT
TCTATGCAAGATGAATCTTCTCAAACTTCTCTTCAAAAAGAAATTTCTACTGAAGAACAA
CTTCGTCGTCTTCAAGAAGAAAAACTTTGTAAAATTTGTATGGATCGTAATATTGCTATT
GTTTTTGTTCCTTGTGGTCATCTTGTTACTTGTAAACAATGTGCTGAAGCTGTTGATAAA
TGTCCTATGTGTTATACTGTTATTACTTTTAAACAAAAAATTTTTATGTCT (SEQ ID NO: 9)
```

```
361 sltrriddti fqnpmvqeai rmgfsfkdik kimeekiqis gsnykslevl vadlvnaqkd
421 smqdessqts lqkeisteeq lrrlqeeklc kicmdrniai vfvpcghlvt ckqcaeavdk
481 cpmcytvitf kqkifms (SEQ ID NO: 10)
```

SNAP25A Non cleavable plus XIAP RING

```
ATGGCTGAAGATGCTGATATGCGTAATGAACTTGAAGAAATGCAACGTCGTGCTGATCAA
CTTGCTGATGAATCTCTTGAATCTACTCGTCGTATGCTTCAACTTGTTGAAGAATCTAAA
GATGCTGGTATTCGTACTCTTGTTATGCTTGATGAACAAGGTGAACAACTTGATCGTGTT
GAAGAAGGTATGAATCATATTAATCAAGATATGAAAGAAGCTGAAAAAAATCTTAAAGAT
CTTGGTAAATGTTGTGGTCTTTTTATTTGTCCTTGTAATAAACTTAAATCTTCTGATGCT
TATAAAAAAGCTTGGGGTAATAATCAAGATGGTGTTGTTGCTTCTCAACCTGCTCGTGTT
GTTGATGAACGTGAACAAATGGCTATTTCTGGTGGTTTTATTCGTCGTGTTACTAATGAT
GCTCGTGAAAATGAAATGGATGAAAATCTTGAACAAGTTTCTGGTATTATTGGTAATCTT
CGTCATATGGCTCTTGATATGGGTAATGAAATTGATACTCAAAATCGTCAAATTAAACGT
ATTATGGAAAAAGCTGATTCTAATAAAACTCGTATTGATGAAGCTAATCAAACTGCTACT
AAAATGCTTGGTTCTGGTTCTCTTACTCGTCGTATTGATGATACTATTTTTCAAAATCCT
ATGGTTCAAGAAGCTATTCGTATGGGTTTTTCTTTTAAAGATATTAAAAAAATTATGGAA
GAAAAAATTCAAATTTCTGGTTCTAATTATAAATCTCTTGAAGTTCTTGTTGCTGATCTT
GTTAATGCTCAAAAAGATTCTATGCAAGATGAATCTTCTCAAACTTCTCTTCAAAAAGAA
ATTTCTACTGAAGAACAACTTCGTCGTCTTCAAGAAGAAAAACTTTGTAAAATTTGTATG
GATCGTAATATTGCTATTGTTTTTGTTCCTTGTGGTCATCTTGTTACTTGTAAACAATGT
GCTGAAGCTGTTGATAAATGTCCTATGTGTTATACTGTTATTACTTTTAAACAAAAAATT
TTTATGTCT (SEQ ID NO: 11)
```

```
maedadmrne leemqrradq ladeslestr rmlqlveesk dagirtlvml deqgeqldrv
eegmnhinqd mkeaeknlkd lgkccglfic pcnklkssda ykkawgnnqd gvvasqparv
vdereqmais ggfirrvtnd arenemdenl eqvsgiignl rhmaldmgne idtqnrqiKr
imckadsnkt ridcanqTat kmlgsg sltrriddti fqnpmvqeai rmgfsfkdik kimeekiqis gsnykslevl vadlvnaqkd
smqdessqts lqkeisteeq lrrlqeeklc kicmdrniai vfvpcghlvt ckqcaeavdk
cpmcytvitf kqkifms (SEQ ID NO: 12)
```

FIG. 8C

SNAP25B Non cleavable plus XIAP RING

```
ATGGCTGAAGATGCTGATATGCGTAATGAACTTGAAGAAATGCAACGTCGTGCTGATCAA
CTTGCTGATGAATCTCTTGAATCTACTCGTCGTATGCTTCAACTTGTTGAAGAATCTAAA
GATGCTGGTATTCGTACTCTTGTTATGCTTGATGAACAAGGTGAACAACTTGAACGTATT
GAAGAAGGTATGGATCAAATTAATAAAGATATGAAAGAAGCTGAAAAAAATCTTACTGAT
CTTGGTAAATTTTGTGGTCTTTGTGTTTGTCCTTGTAATAAACTTAAATCTTCTGATGCT
TATAAAAAAGCTTGGGGTAATAATCAAGATGGTGTTGTTGCTTCTCAACCTGCTCGTGTT
GTTGATGAACGTGAACAAATGGCTATTTCTGGTGGTTTTATTCGTCGTGTTACTAATGAT
GCTCGTGAAAATGAAATGGATGAAAATCTTGAACAAGTTTCTGGTATTATTGGTAATCTT
CGTCATATGGCTCTTGATATGGGTAATGAAATTGATACTCAAAATCGTCAAATTAAACGT
ATTATGGAAAAAGCTGATTCTAATAAAACTCGTATTGATGAAGCTAATCAAACTGCTACT
AAAATGCTTGGTTCTGGTTCTCTTACTCGTCGTATTGATGATACTATTTTTCAAAATCCT
ATGGTTCAAGAAGCTATTCGTATGGGTTTTTCTTTTAAAGATATTAAAAAAATTATGGAA
GAAAAAATTCAAATTTCTGGTTCTAATTATAAATCTCTTGAAGTTCTTGTTGCTGATCTT
GTTAATGCTCAAAAAGATTCTATGCAAGATGAATCTTCTCAAACTTCTCTTCAAAAAGAA
ATTTCTACTGAAGAACAACTTCGTCGTCTTCAAGAAGAAAAACTTTGTAAAATTTGTATG
GATCGTAATATTGCTATTGTTTTTGTTCCTTGTGGTCATCTTGTTACTTGTAAACAATGT
GCTGAAGCTGTTGATAAATGTCCTATGTGTTATACTGTTATTACTTTTAAACAAAAAATT
TTTATGTCT (SEQ ID NO: 13)
```

```
maedadmrne leemqrradq ladeslestr rmlqlveesk dagirtlvml deqgeqleri
eegmdqinkd mkeaeknltd lgkfcglcvc pcnklkssda ykkawgnnqd gvvasqparv
vdereqmais ggfirrvtnd arenemdenl eqvsgiignl rhmaldmgne idtqnrqiKr
imekadsnkt rideanqTat kmlgsg sltrriddti fqnpmvqeai rmgfsfkdik kimeekiqis gsnykslevl vadlvnaqkd
smqdessqts lqkeisteeq lrrlqeeklc kicmdrniai vfvpcghlvt ckqcaeavdk
cpmcytvitf kqkifms (SEQ ID NO: 14)
```

FIG. 8D

DESIGNER UBIQUITIN LIGASES HAVING A NON-CLEAVABLE SNAP25 DOMAIN AND E3-LIGASE DOMAIN

RELATED APPLICATION

This application claims the benefit of U.S. Provisional Application No. 61/060,324, filed Jun. 10, 2008. The entire teachings of the above application are incorporated herein by reference.

BACKGROUND OF THE INVENTION

Intoxication with biological toxins is a serious health and bioterrorism threat problem. Our inability to effectively treat toxin exposure makes certain toxins particularly dangerous agents for terrorist attacks. Treatment options for individuals after toxin infection are limited. For example, once someone is intoxicated with botulinum neurotoxin, the individual is paralyzed for periods up to 4 to 6 months or longer depending on the toxin serotype because the toxin is slow to degrade. During this time the patient is entirely dependent on ventilatory assistance.

Hence, a need exists for an effective treatment after intoxication by toxin. A further need exists for a composition that can inhibit the toxin but also cause the toxin to be degraded to alleviate symptoms of the toxin infection.

SUMMARY OF THE INVENTION

The present invention relates to a recombinant ubiquitin ligase molecule that includes a toxin binding domain that has an affinity for an enzymatically active fragment of one or more toxins or toxin serotypes; and an E3-ligase domain that comprises an E3-ligase or polypeptide that facilitates E2-mediated ubiquitination of the toxin enzymatically active fragment. The toxin binding domain, in an embodiment, can be a non-cleavable SNARE polypeptide or fragment thereof that binds to the enzymatically active fragment of a botulinum neurotoxin (BoNT). In particular, the enzymatically active fragments of BoNT include those known in the art or from later discovered serotypes, such as BoNT serotypes A-G. Examples of SNARE polypeptides include a non-cleavable SNAP-25, syntaxin, or synaptobrevin. In another embodiment, wherein the toxin binding domain includes a G protein $\alpha_s$ polypeptide or fragment thereof that has affinity to the enzymatically active fragment of a cholera toxin. The toxin binding domain that has an affinity for an enzymatically active fragment of one or more of the following toxins The toxin includes, botulinum neurotoxin (BONT) (serotypes A-G), Clostridia difficile toxins A and B (Tcd A and Tcd B), Clostridium Lethal Toxin, Anthrax Lethal Factor (LF), Ricin, Exotoxin A, Diphtheria toxin, Cholera toxin, Tetanus toxin, Shiga toxin, and any combinations thereof In one aspect, a polypeptide that facilitates E2-mediated ubiquitination is an antibody specific to E2. Another aspect of the invention includes a recombinant ubiquitin ligase having one or more of the following E3 ligase domains: RING, HECT, U-box, RIBRR, F-box domain, DCAF domain, DDS2, HIF-mimetic peptides, IkB-mimetic sequences, BTB domain or combination thereof.

In particular, the recombinant ubiquitin ligase molecule of the present invention includes a non-cleavable SNARE polypeptide or fragment thereof is encoded by a nucleic acid molecule that comprises one or more of the following nucleic acid sequences: a nucleic acid sequence having greater than or equal to about 70% identity with SEQ ID NO: 5; a nucleic acid sequence complement having greater than or equal to about 70% identity with of SEQ ID NO: 5; a nucleic acid molecule having greater than or equal to about 70% identity with a molecule that hybridizes to SEQ ID NO: 5; and a nucleic acid sequence that encodes an amino acid sequence having greater than or equal to about 70% similarity to a sequence set forth in SEQ ID NO: 6. Similarly, the present invention further relates to a recombinant ubiquitin ligase molecule, wherein the non-cleavable SNARE polypeptide or fragment thereof that comprises one or more of the following amino acid sequences: an amino acid sequence encoded by a nucleic acid having greater than or equal to about 70% identity with SEQ ID NO: 5; an amino acid sequence encoded by a complement having greater than or equal to about 70% identity with of SEQ ID NO: 5; an amino acid sequence encoded by a nucleic acid molecule having greater than or equal to about 70% identity with a molecule that hybridizes to SEQ ID NO: 5; and an amino acid sequence having greater than or equal to about 70% similarity to a sequence set forth in SEQ ID NO: 6.

The recombinant ubiquitin ligase molecule of the present invention includes a SNARE polypeptide or fragment that has been mutated to be non-cleavable. In particular, the molecule of the present invention is encoded by a nucleic acid molecule that comprises one or more of the following nucleic acid sequences: a nucleic acid sequence having greater than or equal to about 70% identity with SEQ ID NO: 1 or 3; a nucleic acid sequence complement having greater than or equal to about 70% identity with of SEQ ID NO: 1 or 3; a nucleic acid molecule having greater than or equal to about 70% identity with a molecule that hybridizes to SEQ ID NO: 1 or 3; and a nucleic acid sequence that encodes an amino acid sequence having greater than or equal to about 70% similarity to a sequence set forth in SEQ ID NO: 2 or 4. These nucleic acid molecules include one or more mutations to render the polypeptide non-cleavable. Along the same lines, the present invention relates to a recombinant ubiquitin ligase molecule that comprises one or more of the following amino acid sequences: an amino acid sequence encoded by a nucleic acid having greater than or equal to about 70% identity with SEQ ID NO: 1 or 3; an amino acid sequence encoded by a complement having greater than or equal to about 70% identity with of SEQ ID NO: 1 or 3; an amino acid sequence encoded by a nucleic acid molecule having greater than or equal to about 70% identity with a molecule that hybridizes to SEQ ID NO: 1 or 3; and an amino acid sequence having greater than or equal to about 70% similarity to a sequence set forth in SEQ ID NO: 2 or 4; wherein the nucleic acid molecule comprises one or more mutations to render the polypeptide non-cleavable.

The present invention pertains to a recombinant ubiquitin ligase molecule having a E3 ligase domain that is encoded by a nucleic acid molecule that comprises one or more of the following nucleic acid sequences: a nucleic acid sequence having greater than or equal to about 70% identity with SEQ ID NO: 9; a nucleic acid sequence complement having greater than or equal to about 70% identity with of SEQ ID NO: 9; a nucleic acid molecule having greater than or equal to about 70% identity with a molecule that hybridizes to SEQ ID NO: 9; and a nucleic acid sequence that encodes an amino acid sequence having greater than or equal to about 70% similarity to a sequence set forth in SEQ ID NO: 10. Similarly, the present invention includes a recombinant ubiquitin ligase molecule having a E3 ligase domain that comprises one or more of amino acid sequences: an amino acid sequence encoded by a nucleic acid having greater than or equal to about 70% identity with SEQ ID NO: 9; an amino acid sequence encoded by a complement having greater than or equal to about 70% identity with of SEQ ID NO: 9; an amino acid sequence encoded by a nucleic acid molecule having greater than or equal to about 70% identity with a molecule that hybridizes to SEQ ID NO: 9; and an amino acid sequence having greater than or equal to about 70% similarity to a sequence set forth in SEQ ID NO: 10.

Additionally, the present invention relates to a recombinant ubiquitin ligase molecule that is encoded by a nucleic acid molecule that comprises one or more of the following nucleic acid sequences: a nucleic acid sequence having greater than or equal to about 70% identity with SEQ ID NO: 11 or 13; a nucleic acid sequence complement having greater than or equal to about 70% identity with of SEQ ID NO: 11 or 13; a nucleic acid molecule having greater than or equal to about 70% identity with a molecule that hybridizes to SEQ ID NO: 11 or 13; and a nucleic acid sequence that encodes an amino acid sequence having greater than or equal to about 70% similarity to a sequence set forth in SEQ ID NO: 12 or 14. Also, the present invention includes a recombinant ubiquitin ligase molecule that comprises one or more of the following amino acid sequences: an amino acid sequence encoded by a nucleic acid having greater than or equal to about 70% identity with SEQ ID NO: 11 or 13; an amino acid sequence encoded by a complement having greater than or equal to about 70% identity with of SEQ ID NO: 11 or 13; an amino acid sequence encoded by a nucleic acid molecule having greater than or equal to about 70% identity with a molecule that hybridizes to SEQ ID NO: 11 or 13; and an amino acid sequence having greater than or equal to about 70% similarity to a sequence set forth in SEQ ID NO: 12 or 14.

The present invention pertains to an isolated polypeptide molecule that includes a non-cleavable SNARE polypeptide or fragment thereof that has affinity to the enzymatically active fragment of a BoNT; a BoNT holotoxin, wherein the BoNT holotoxin comprises a deletion in the light chain, a mutation of the heavy chain, or both, wherein the deletion, mutation or both renders BoNT holotoxin atoxic; and an E3-ligase domain that comprises an E3-ligase or polypeptide that facilitates E2-mediated degradation of the toxin enzymatically active fragment of a BoNT. The non-cleavable SNARE polypeptide and the BoNT atoxic holotoxin can be fused e.g., the non-cleavable SNARE polypeptide or fragment thereof is fused to the N-terminus of the BoNT atoxic holotoxin. The present invention further relates to fusion proteins that include the isolated polypeptide of the present invention.

In yet another embodiment, the recombinant ubiquitin ligase molecule of the present invention relates to a non-cleavable SNARE polypeptide or fragment thereof that has affinity to the enzymatically active fragment of a BoNT; an E3-ligase domain that comprises an E3-ligase or polypeptide that facilitates E2-mediated ubiquitination of the toxin enzymatically active fragment; and a translocation/cellular binding domain. The translocation/cellular binding domain binds to the cellular membrane of a cell and delivers the recombinant ubiquitin ligase into the cell. Examples of the translocation/cellular binding domain include an antennapedia protein, HIV TAT protein, herpes simplex virus VP22 protein, penetratin-derived peptides, kFGF, human β3 integrin, L- and D-arginine oligomers, $SCWK_n$, $(LARL)_n$, HA2; RGD; $K_1$ 6RGD oligomer; $AlkCWK_{18}$, DiCWK18, DipaLytic; Plae, Kplae, MPG peptide, Pep-1, or an atoxic neurotoxin.

Methods of degrading or inhibiting one or more BoNT serotypes that have intoxicated one or more cells are include in the present invention. The steps of the method include contacting an amount of the recombinant ubiquitin ligase of the present invention with the intoxicated cells; wherein the recombinant ubiquitin ligase degrades or inhibits at least one BoNT serotype. An amount of recombinant ubiquitin ligase ranges from e.g., about 1 pM to about 100 mM. The time for contacting the designer ligase of the present invention with intoxicated cells ranges from about 1 minute and about 1 week.

The present invention also relates to methods of treating an individual having one or more cells intoxicated with one or more BoNT serotypes. The steps of the present invention include administering to the individual an amount of recombinant ubiquitin ligase of present invention in a carrier; wherein one or more symptoms associated with BoNT intoxication are reduced or reversed. One or more symptoms associated with BoNT intoxication that are reduced or revised include blurred vision, dry mouth, difficulty swallowing, difficulty speaking, paralysis, muscle weakness; respiratory failure, and decreased nerve conduction. The amount of recombinant ubiquitin ligase administered to the individual ranges from e.g., about 10 ng to about 5 gm. The recombinant ubiquitin ligase can be administered intravenously, parenterally, orally, nasally, by inhalation, by implant, by injection, or by suppository, and can be administered once or periodically. Additionally, the present invention relates to pharmaceutical compositions comprising the recombinant ubiquitin ligase molecule of the present invention and a carrier.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2 is a schematic diagram of designer E3 ligases that target toxins for proteasome degradation.

FIG. 4 is a schematic showing the use of Non-cleavable SNAP25 (SNAP25/NC) as targeting domains, and a seven different E3 domains: RING, HECT, IkB, HIF, U-Box, RIBRR and TrCP.

FIG. 5 is a schematic diagram of a designer E3 ligase having non-cleavable (NC) SNAP-25 fused to a Ring E3 domain.

FIG. 6A is a photograph of a Western Blot following immunoprecipitation to assess ubiquitin modification probed with anti-GFP and anti-Ubi antibodies against SNAP-25/NC control or SNAP-25/NC-RING in cells transfected with YFP-BoNT/A LC (Light Chain).

FIG. 6B is a photograph of a Western Blot to assess ubiquitin modification probed with an anti-GFP antibody against SNAP-25/NC control or SNAP-25/NC-RING in cells transfected with YFP-LCA.

FIG. 7 is a graph showing that designer E3 ligase accelerates BoNT/A LC turnover in N18 cells.

FIGS. 8A-D are a drawing depicting the following sequences: SNAP25A nucleic acid (SEQ ID NO: 1) and amino acid (SEQ ID NO: 2) sequences; SNAP25B nucleic acid (SEQ ID NO: 3) and amino acid (SEQ ID NO: 4) sequences; mutated non-cleavable SNAP-25A and B nucleic acid (SEQ ID NO: 5) and amino acid (SEQ ID NO: 6) sequences; Full length XIAP nucleic acid (SEQ ID NO: 7) and amino acid (SEQ ID NO: 8) sequences; RING domain nucleic acid (SEQ ID NO: 9) and amino acid (SEQ ID NO: 10) sequences; SNAP25A/NC with XIAP RING domain nucleic acid (SEQ ID NO: 11) and amino acid (SEQ ID NO: 12) sequences; SNAP25B Non cleavable plus XIAP RING nucleic acid (SEQ ID NO: 13) and amino acid (SEQ ID NO: 14) sequences.

DETAILED DESCRIPTION OF THE INVENTION

Figure 1:
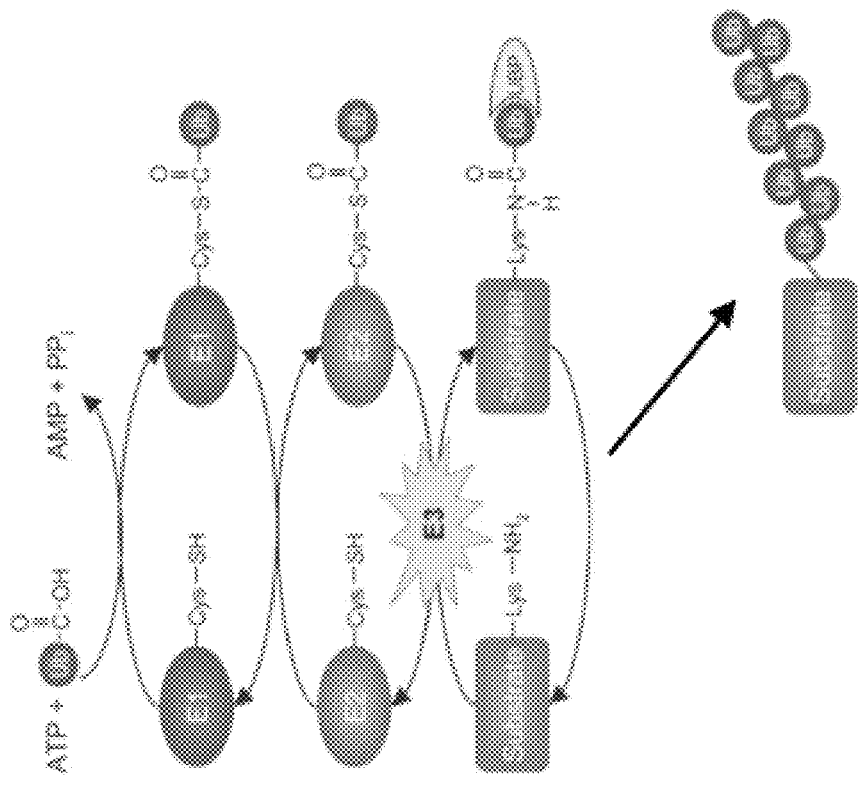
FIG. 1 is a schematic diagram showing ubiquitin proteasome system.

A description of preferred embodiments of the invention follows.

The present invention relates to a recombinant ubiquitin ligase molecule, also referred to herein as a "designer ubiquitin ligase". In one aspect, the molecule of the present invention has at least two domains: a toxin binding domain that is specific for the enzymatically active portion of a toxin, referred to herein as the "toxin active fragment", and an E3 ligase domain that facilitates E2-mediated ubiquitination. See FIG. 1. Such a designer ligase allows the molecule to bind to the enzymatically active portion of the toxin and inhibit its action, while the E3 ligase domain allows for the ubiquitination and subsequent degradation of the toxin. In another embodiment, the composition of the present invention includes another domain, a Translocation/Cell Binding domain, which allows the molecule to bind to the cellular membrane and then be transported into the cell e.g., a delivery vehicle. Accordingly, the present invention relates to the composition as well as methods for inhibiting and/or degrading one or more toxins.

The Toxin Binding Domain and The Toxin:

The present invention relates to a toxin binding domain that has an affinity to or binds to the enzymatically active portion of a toxin. The enzymatically active portion of the toxin is referred to herein as a "toxin active fragment." The toxin active fragment can be from any toxin known or later discovered or developed. A toxin is a molecule, generally produced by a living cell or organism, which gets into the cell and causes disease or injury. Certain toxins come from animals such as spiders, snakes, pufferfish, scorpions, jellyfish, snails, and bees. Types of toxins include, e.g., neurotoxins (e.g., Botulinum neurotoxin), hemotoxins, necrotoxins, cyanotoxins, plant toxins, and mycotoxins. A neurotoxin is a toxin that affects neurons. Several toxins generally interact with membrane proteins such as ion channels (e.g., sodium, potassium, or calcium channels). A common effect is paralysis, which often sets in very rapidly. Examples of neurotoxins include botulinum neurotoxin (BoNT), tetanospasmin, tetrodotoxin, and conotoxins. Other protein toxins implicated by the invention are Tcd A and B, Clostridium Lethal Toxin, Anthrax Lethal Factor, Ricin, Exotoxin A, Diphtheria toxin, Cholera toxin, Tetanus toxin, Shiga toxin, and a combination thereof.

In an embodiment, BoNT or an enzymatically active portion thereof is used. BoNT is a neurotoxin protein produced by the bacterium, *Clostridium botulinum*. There are at least seven different BoNT serotypes (A to G), and some of the serotypes have various isotypes (e.g., three isotypes of serotype A have been described). Generally, the BoNT has two chains, a heavy chain (e.g., about 100-kDa) and a light chain (e.g., about 50-kDa ) joined by a disulfide bond. The heavy chain contains a cell binding domain and a translocation domain that allows for the toxin to bind to and enter the cell; this heavy chain portion will be referred to as a cell-binding/translocation domain. The light chain is an enzyme (e.g., a protease) that cleaves a fusion protein (e.g., SNAP-25, syntaxin or synaptobrevin) at a neuromuscular junction, preventing vesicles from anchoring to the membrane to release acetylcholine. By inhibiting acetylcholine release, the toxin interferes with nerve impulses to cause muscle contraction causing the paralysis of muscles, seen in botulism.

The toxin binding domain can bind to a toxin active fragment that has been derivative from a toxin's enzymatically active portion. A "derivative" refers to a molecule with toxin enzymatic activity but contains one or more chemical or functional alterations thereof, as compared to the native enzymatic portion. For instance, the botulinum toxin light chain can be modified so that one or more of its amino acid residues is deleted, modified, replaced, or truncated. For instance, the botulinum toxin light chain can be modified in a way such that, for instance, the modification enhances its properties or decreases undesirable side effects, but that still retains the desired botulinum toxin activity. The botulinum toxin can be derived from any of the botulinum toxin serotypes and/or isoforms produced by the bacterium. Alternatively, the botulinum toxin can be a toxin prepared using recombinant or synthetic chemical techniques (e.g., a recombinant peptide, a fusion protein, or a hybrid neurotoxin, as prepared from subunits or domains of different botulinum toxin serotypes). Additionally, the botulinum toxin active fragment can be in the form of a botulinum toxin precursor, which can itself be non-toxic, for instance a non-toxic zinc protease that becomes toxic on proteolytic cleavage.

"Enzymatically active" portion of the toxin refers to the portion of the toxin that normally gets inside of the cell (e.g., in the endosome or cytosol) and is active. Toxins are often made up of at least two parts, a cell-binding/translocation domain, and an enzymatically active domain. In the BoNT, the enzymatically active domain is often referred to as the "light chain." However, the enzymatically active domain for other toxins can have other names. For example, with the ricin toxin, the enzymatically active domain is the "A" Chain. The cell-binding domain and translocation domain, referred to as the cell-binding/translocation domain, facilitate binding of the toxin active fragment to the cell membrane and transporting the toxin active fragment across the cellular membrane. For certain toxins like the BoNT, this domain is referred to as the heavy chain. For other toxins, such as ricin, this is referred to as the B Chain.

In an embodiment, enzymatically active refers to a protein that causes the cleavage of one or more proteins in the cell, which in turn causes toxic effects. In the case of certain toxins, the enzymatically active domain cleaves a SNARE ("Soluble NSF Attachment Receptor") protein. SNARE proteins are a large protein superfamily consisting of several members. The primary role of SNARE proteins is to mediate fusion of cellular transport vesicles with the cell membrane. The core SNARE complex is formed by four a-helices contributed by synaptobrevin, syntaxin and SNAP-25. Different toxins, serotypes of a certain toxin, or cell types will involve cleavage of different SNARE proteins. Tetanospasmin, e.g., is the neurotoxin produced by the vegetative spore of *Clostridium tetani* and causes tetanus. BoNT A, C, and E cleave SNAP-25, in addition BoNT C cleaves syntaxin 1. BoNT B, D, F, G and tetanus toxin cleave VAMP-2. More than one SNARE protein can be cleaved by a single toxin active fragment.

Botulinum toxin is a zinc-dependent protease. As described herein, enzymatic activity resides generally in the light chain of the molecules. These enzymes cleave SNARE proteins, synaptobrevin 1 and 2, syntaxin and SNAP 25, which form the core of a complex involved in the fusion of transmitter-containing vesicles with the plasma membrane. Prior to fusion, the SNARE proteins in the vesicle and plasma membrane interact forming a complex which contracts with an increase in the intracellular calcium concentration, pulling the vesicle close to the plasma membrane. Interaction between lipids in the two membranes allows the vesicle and nerve terminal active zone to fuse. During this fusion, the contents of the vesicles, mainly neurotransmitters, are released, and the inner surface of the vesicles is exposed to the synaptic cleft. If one of the SNARE proteins is cleaved by a neurotoxin, complex formation cannot occur and fusion is interrupted.

The present invention further involves using a non-cleavable recombinant SNARE protein as the toxin binding domain. Any one of the SNARE proteins can be made non-cleavable using DNA recombinant technology. The non-cleavable SNARE protein can be made non-cleavable with mutations, deletion and/or truncations in the sequence. The sequence is altered so the molecule is non-cleavable by the toxin, but still binds to the light chain or enzymatically active fragment of the toxin. A non-cleavable SNARE endoprotease can bind the toxin active fragment, but will not be cleaved, thereby rending the light chain inactive. Since the non-cleavable SNARE also has an E3-ligase domain, the toxin is ubiquitinated and degraded. Various E3 domains for use in the designer ligase of the present invention are described herein. Additionally, methods for mutating, truncating and deleting nucleic acid sequences are described herein.

As described above, a SNARE endoprotease includes SNAP25A and B. FIG. 8A shows the nucleic acid sequences, SEQ ID NO: 1 and 3, and amino acid sequences, SEQ ID NO: 2 and 4, respectively. Using recombinant technologies, to render these sequences non-cleavable, the sequences were mutated, in one embodiment, as shown in FIG. 8A in SEQ ID NO: 5 and 6. This portion of the sequence (the latter 49 amino acids) is common to both SNAP25A and B and these mutations render both sequences non-cleavable. Other mutations can be used to render these sequences non-cleavable. Hence, in an embodiment, the claimed polypeptide of the present invention includes SEQ ID NO: 6, or is encoded by SEQ ID NO: 5.

Another polypeptide that can be used as the toxin binding domain is the G protein $\alpha_s$ molecule implicated with the Cholera Toxin. The enzymatically active fragment of the Cholera toxin, the A1 fragment of the toxin A subunit enters the cytosol, where it activates the G protein $\alpha_2$ through an ADP-ribosylation reaction. By fusing this protein to an E3 domain, and optionally to a delivery system, the designer ubiquitin ligase of the present invention can bind to the enzymatically active portion of the toxin and facilitate ubiquitination of the cholera toxin.

With respect to the BoNT serotypes, the light chain for each serotype has an amino acid sequence, or is encoded by a nucleic acid sequence. The present invention specifically relates a toxin binding domain that binds to the light chain of any of the BoNT serotypes, as well as any recombinant, mutated, truncated or deleted portions thereof. As such, the toxin active fragment can be the recombinant form of any enzymatically active portion thereof (e.g., the light chain of a BoNT serotype).

The toxin binding domain can be made from recombinant DNA which transcribes the desired amino acid sequence that is specific to the toxin active fragment. The recombinant nucleic acid sequence can be a nucleotide "variant" of a toxin binding domain. A variant is a sequence that differs from the known nucleotide sequence for that molecule in having a truncation, and/or one or more nucleotide deletions, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C. The specific sequences, variants of the toxin binding domain are further described herein.

E3 Ligase Domain That Facilitates E2-mediated Ubiquitination

An embodiment of present invention relates to a designer ubiquitin ligase or recombinant ubiquitin ligase that includes the toxin binding domain, as described herein and an E3 ligase domain. The E3 ligase domain facilitates ubiquitination of the complex. Ubiquitination occurs, in an embodiment, when an E2 enzyme interacts with a specific E3 partner and transfers the ubiquitin to the toxin active fragment. FIG. 1. In some cases, it receives the ubiquitin from the E2 enzyme and transfers it to the target protein; in other cases, it acts by interacting with both the E2 enzyme and the toxin active fragment, but never itself receives the ubiquitin. With respect to the present invention, the toxin binding domain of the designer ubiquitin ligase binds to the toxin to form a complex between the polypeptide of the present invention and the toxin active fragment, and the E3 ligase domain allows for ubiquitination of the complex, which leads to the toxin's degradation.

Figure 3:
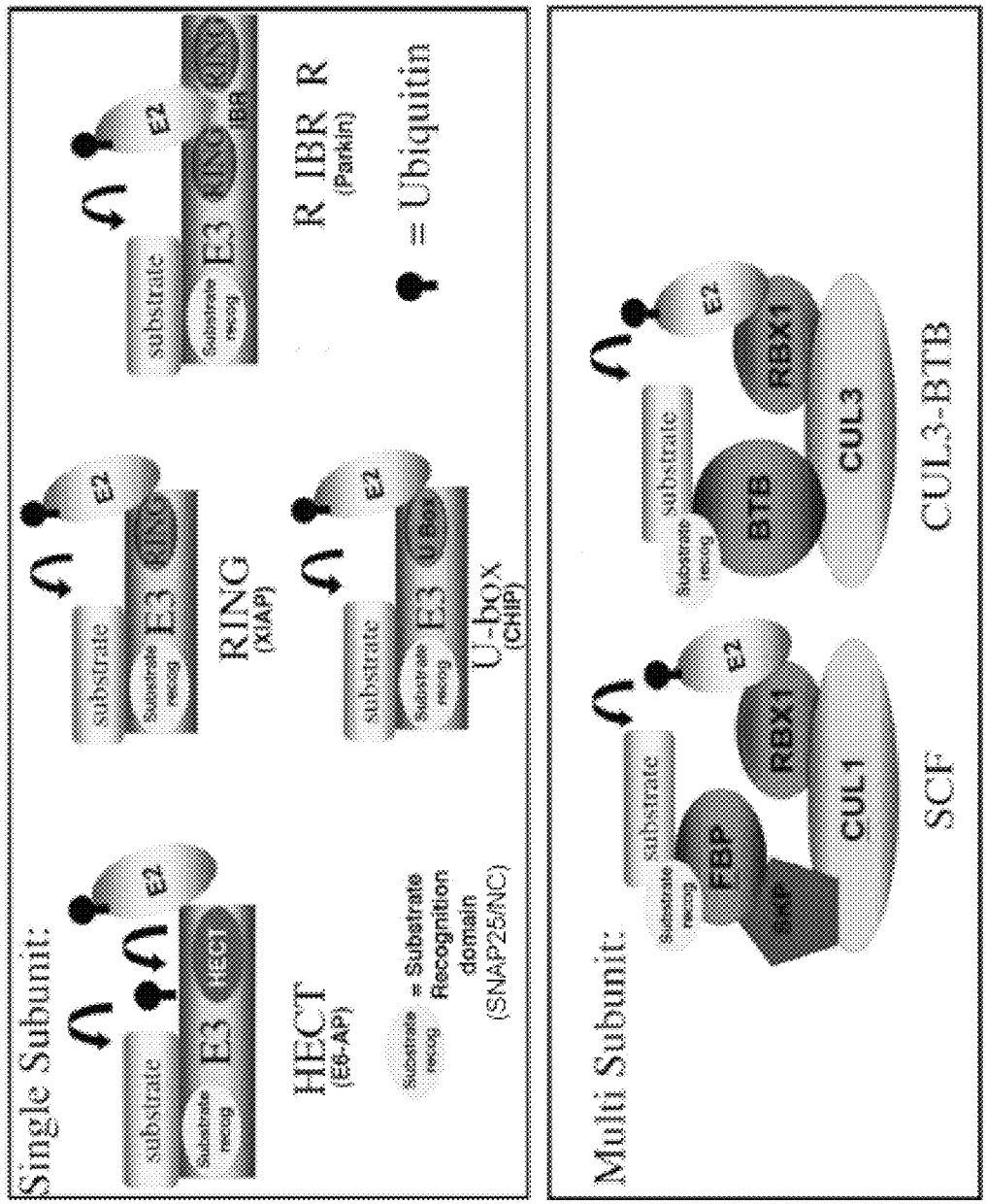
FIG. 3 is a schematic diagram of the following ubiquitin design ligase single and multiunit constructs that include the following E3 domains: HECT, RING R IBR R, U-BOX, SCF and BTB.
Figure 5:
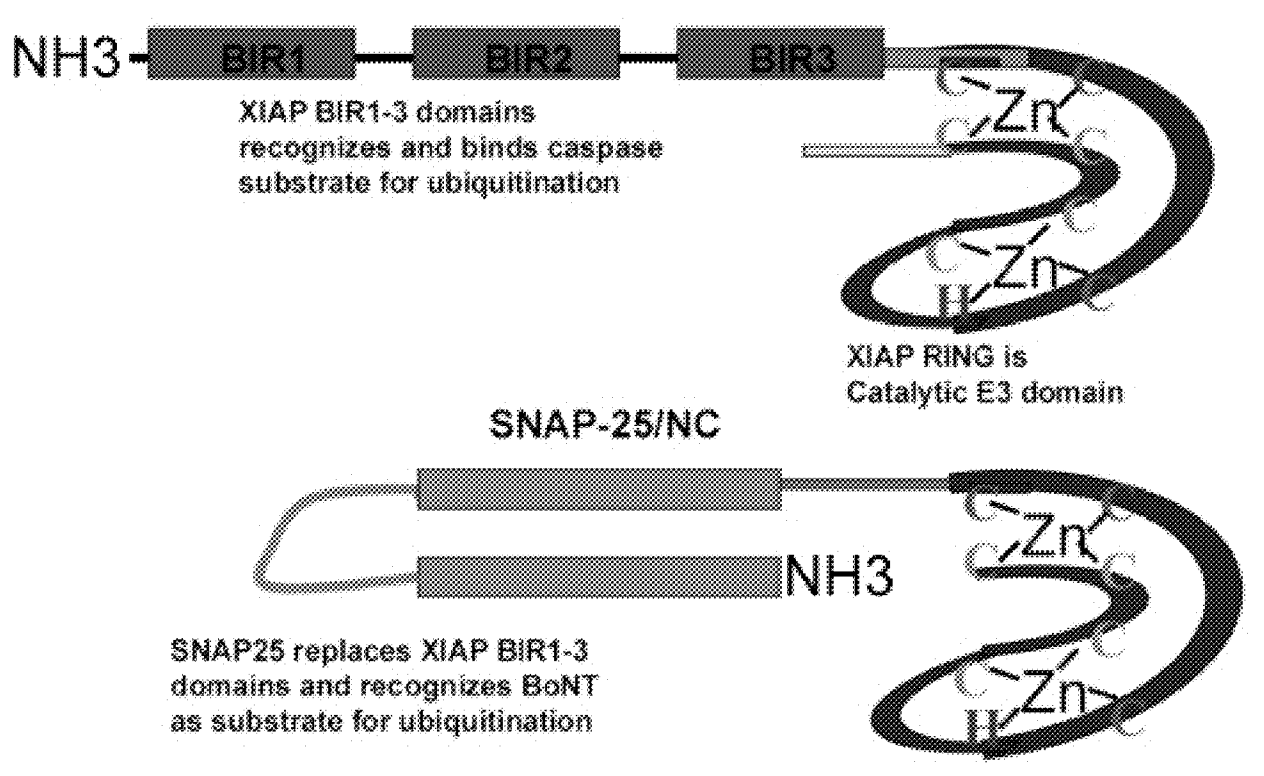

In particular, an E3 ligase can be a multimeric protein complex or a single chain protein that includes various complexes such as E2 binding domains. Examples of various E3 ligase domains include one or more RING, HECT, U-box, RIBRR, F-box domain, DCAF domain, DDS2, HIF-mimetic peptides, IkB-mimetic sequences, BTB domain, or combination thereof. FIG. 3 shows a number of single and multi subunit constructs in which the E3 ligase domains used are a HECT, RING, R IBR R, SCF, and BTB. The protein from which the domains are derived are in parenthesis in the figure. For example, the HECT domain is derived from the E6-AP protein, the RING is derived from the XIAP protein, and the R IBR R domain is from the Parkin protein. For example, FIG. 5 shows how the RING domain of the XIAP protein is cleaved to separate the RING domain from the BIR1-3 domains. The RING is fused, in this case, to a non-cleavable SNAP-25 molecule, which recognizes BoNT as a substrate for ubiquitination. Additionally, by way of example, the full length XIAP nucleic acid (SEQ ID NO: 7) and amino acid (SEQ ID NO: 8) are shown in FIG. 8B. The RING portion, SEQ ID NOs: 9 and 10 are shown in FIG. 8C. When the RING domain, SEQ ID NO: 10 is fused with non-cleavable SNAP25A, (See SEQ ID NOs: 2 and 6), the resulting sequence is SEQ ID NO: 12, a non-cleavable SNAP25-RING construct or fusion protein. The corresponding nucleic acid sequence is shown as well as SEQ ID NO: 11. Similarly, the noncleavable SNAP25B protein fused with the RING domain is shown as SEQ ID NOs: 13 and 14 in FIG. 8D.

FIG. 4 shows several of E3 ligase domains fused to non-cleavable SNAP-25 that were made as fusion proteins, and include a non-cleavable SNAP25 fused to a RING, HECT, IkB, HIF, U-box, RIBRR, and/or TrCP. These fusion proteins were fused to a Yellow Fluorescent Protein (YFP) so that the fusion proteins can be expressed and detected.

These E3 ligase domains facilitate ubiquitination, and when fused with the toxin binding domain that is specific to the enzymatically active portion of the toxin, allows for the degradation of the toxin active fragment. Any E3 ligase domains including E2 binding domains known or later discovered or developed can be used. Recombinant E3 ligase domains can be used. Known E3 ligase-binding domains can be modified to increase its ability to induce ubiquitination and bind to E2. As described herein, proteins and their nucleic acids can be modified and expressed.

Figure 2:
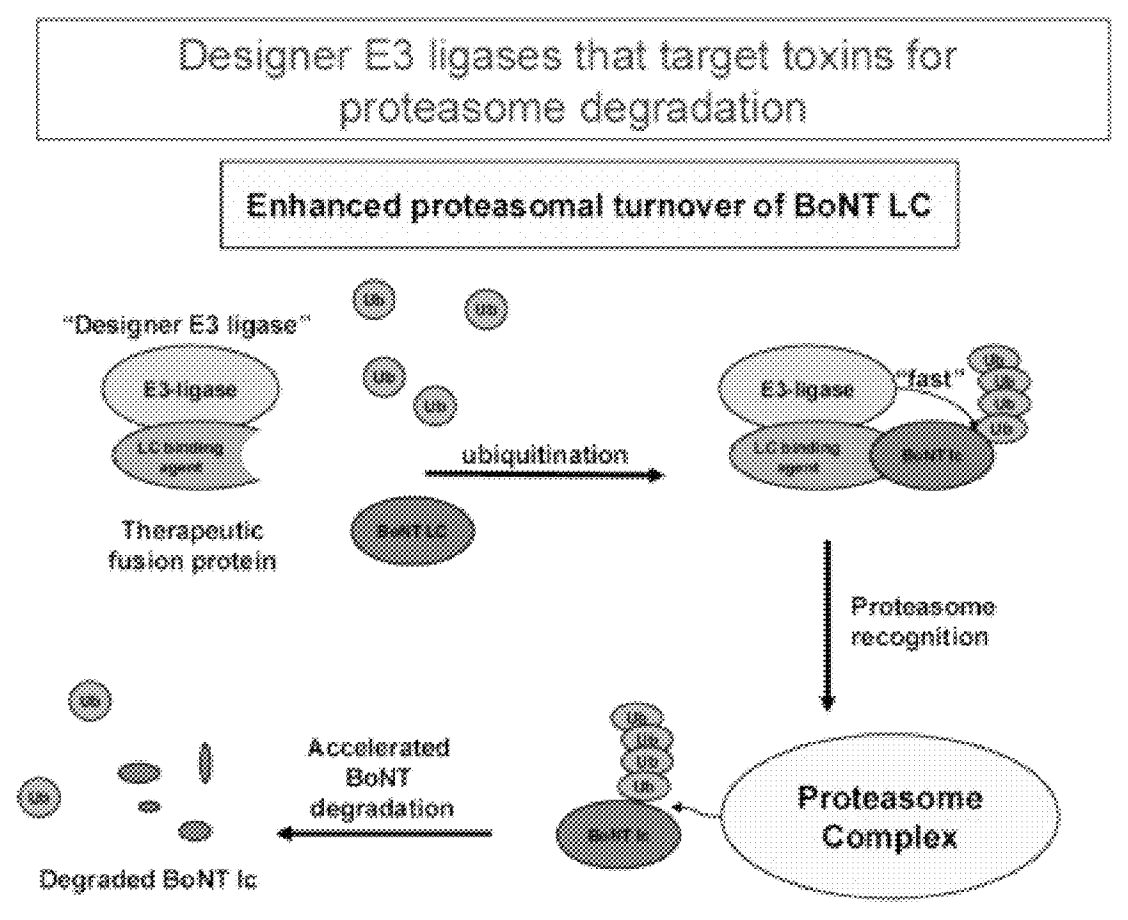

"Facilitating ubiquitination" refers to aiding or assisting in the attachment of one or more ubiquitin monomers via E2, which in turn, serves as a recognition site for proteasomal degradation. See FIG. 1. Without ubiquitination, the toxin will eventually degrade but takes a longer time, as compared to degradation via the ubiquitin process. Accordingly, the presence of the E3 ligase, in an embodiment, allows for faster degradation of the toxin, as compared to degradation of the toxin via a non-polyubiquitination process. See FIG. 2. FIG. 7 shows that non-cleavable SNAP-25 fused to a RING domain substantially accelerated proteasome-mediated degradation of recombinant BoNT/A in transfected neurons.

In an embodiment, the present invention relates an E3 ligase domain that is an antibody or antibody fragment that binds E2. The term "antibody fragment" refers to portion of an immunoglobulin having specificity to E2 or a molecule involved with its function. The term, "antibody fragment", is intended to encompass fragments from both polyclonal and monoclonal antibodies including transgenically produced antibodies, single-chain antibodies (scFvs), recombinant Fabs, heavy-chain-only antibodies, and specifically recombinant shark or camelid single chain antibodies (VHHs). VHHs are also referred to as nanobodies.

Nanobodies are antibody-derived therapeutic proteins that contain the unique structural and functional properties of naturally-occurring heavy-chain antibodies. The Nanobody technology is based on fully functional antibodies from camelids that lack light chains. These heavy-chain antibodies contain a single variable domain (VHH) and two constant domains (CH2 and CH3). The cloned and isolated VHH domain is a stable polypeptide harboring the antigen-binding capacity of the original heavy-chain antibody. (Ablynx, Ghent, Belgium).

Suitable methods of producing or isolating antibody fragments of the requisite specificity are known in the art and include for example, methods which select recombinant antibody from a library, by PCR.

Functional fragments of antibodies, including fragments of chimeric, humanized, primatized, veneered or single chain antibodies, can also be produced. Functional fragments or portions of the foregoing antibodies include those which are reactive with E2. For example, antibody fragments capable of binding to E2 include, but not limited to, scFvs, Fabs, VHHs, Fv, Fab, Fab' and F(ab')$_2$ are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain. Accordingly, the present invention encompasses a polynucleic acid that encodes the an antibody that binds E2.

Delivery Vehicles Translocation and Cellular Binding Domains

In an embodiment of the present invention, the designer ubiquitin ligase has a translocation and cell binding domain that binds to the cellular membrane of a cell and delivers the polypeptide molecule into the cell. This domain is also referred to as a "delivery vehicle" and can be used interchangeably. The translocation and cellular binding (TCB) domain, in an embodiment, is fused or otherwise attached, directly or indirectly, to the toxin binding domain, as described herein. The polypeptide of the present invention and further include the E3 ligase domain, also described herein.

In an embodiment, the TCB domain can be the heavy chain, chain "B" or the otherwise cell binding/translocation domain of a toxin. For example, the following domains can be used as the TCB domain: BoNT serotype, or an atoxic Tcd A or B. The heavy chain of a toxin can bind the cellular membrane of the intoxicated cell, and allow the transport of the molecule of the present invention to the inside of the cell.

In yet another embodiment, an atoxic holotoxin can be used to deliver the molecule of the present invention into the cell. A holotoxin is the entire toxin, both the light (e.g., the enzymatically active portion) and heavy (e.g., the TCB portion) chains of the toxin. An atoxic holotoxin refers to a molecule having both chain types, but mutated so that the light chain is no longer enzymatically active. Atoxic holotoxins can be mutated or deleted in any number of ways using methods known in the art. In the BoNT embodiment, serotype A is mutated/truncated to render the light chain enzymatically inactive. In a certain embodiment, portions of the light chain are deleted or truncated to render it inactive. In yet another embodiment, the heavy chain of the toxin can further be mutated, altered, and/or truncated. Methods of altering nucleic acid molecule are further described herein. The use of one type of delivery system that utilizes mutated light chain BoNT holotoxin is described in U.S. Pat. No. 6,203,794.

The composition of the present invention, the TCB domain can be, for example, covalently linked to the toxin binding domain and/or the E3 ligase domain and further can be, for example, a protein, peptide or peptidomimetic. In one embodiment, the composition of the present invention is a chimeric protein, peptide or peptidomimetic in which the delivery agent is operatively fused having e.g., a length of at most 50 or 100 residues.

A variety of TCB domains can be covalently linked to the toxin binding domain and/or E3 ligase domain and include, e.g., an antennapedia protein or active fragment thereof, such as an active fragment having the amino acid sequence RQIKIWFQNRRMKWKK (SEQ ID NO: 15); an HIV TAT protein or active fragment thereof, such as an active fragment having the amino acid sequence YGRKKRRQRRR (SEQ ID NO: 16); or a herpes simplex virus VP22 protein or active fragment thereof.

In general, in the composition of the present invention, TCB domain can be, for example, covalently linked to the domains described herein, as a protein, peptide or peptidomimetic. In one embodiment, the present invention is a chimeric protein, peptide or peptidomimetic in which the delivery agent is operatively fused to the toxin binding domain and/or E3 ligase domain. Such a composition can be, for example, a peptide or peptidomimetic having a length of at most 50 or 100 residues. Examples of penetratin-derived peptides that are useful as delivery agents include SEQ ID NO: 17 (RQIKIWFQNRRMKWKK), SEQ ID NO:18 (KKWKMRRNQFWIKIQR); SEQ ID NO: 19 (RQIKIWFQNRRMKWKK); SEQ ID NO: 20 (RQIKIWFPNRRMKWKK); SEQ ID NO:21 (RQPKIWFPNRRMPWKK); SEQ ID NO: 22 (RQIKIWFQNMRRKWKK); SEQ ID NO: 23 (RQIRIWFQNRRMRWRR); and SEQ ID NO:24 (RRWRRWWRRWWRRWRR).

In another embodiment, the composition of the present invention includes a delivery agent which is a HIV transactivator (TAT) protein or an active fragment thereof. Such a delivery agent can include, for example, a sequence identical or similar to residues 47-57 or 47-59 of HIV TAT. As an example, fusion proteins including residues 47-57 of HIV TAT (YGRKKRRQRRR; SEQ ID NO:25) cross the plasma membrane of, for example, human and murine cells in vitro and in vivo; a variety of proteins from 15 to 120 KDa have been shown to retain biological activity when fused to a HIV TAT delivery agent. An HIV TAT delivery agent can be positively charged and can function, for example, in an energy-, receptor-, transporter- and endocytosis-independent manner to deliver a covalently linked toxin binding domain and/or E3 ligase domain to cells intoxicated with a toxin.

Yet another TCB domain for use with the present invention includes a herpes simplex virus VP22 protein or active fragment thereof. In a particular embodiment, the composition of the present invention includes an HSV type 1 (HSV-1) VP22 protein or active fragment thereof. HSV VP22, a nuclear transcription factor, can cross the plasma membrane through non-classical endocytosis and can enter cells independent of GAP junctions and physical contacts. As a fusion with a variety of different proteins, HSV VP22 results in uptake into cells of different types including terminally differentiated cells and can function to deliver a linked toxin binding domain and/or E3 ligase domain.

An example of another delivery agent useful in the present invention corresponds to or is derived from a hydrophobic signal sequence. Such a delivery agent can be, for example, the Kaposi fibroblast growth factor (kFGF) or an active fragment thereof such as AAVALLPAVLLALLAP (SEQ ID NO:26); human β3 integrin or an active fragment thereof; or another hydrophobic delivery agent known in the art.

A delivery agent that can form a portion of the composition of the present invention also can be a synthetic sequence that shares one or more characteristics of a naturally occurring delivery agent such as a protein transduction domain (PTD). Such delivery agents include, but are not limited to, L- and D-arginine oligomers, for example, 9-mers of L- or D-arginine and related peptoids. Such delivery agents further include basic peptides and peptidomimetics; basic α-helical peptides and peptidomimetics; and peptides and peptidomimetics with optimized arginine alignment or optimized a-helical character as compared to a naturally occurring protein transduction domain such as residues 47-57 of HIV TAT. See, for example, WO 99/29721. Additional examples of delivery agents useful in the invention include SCWK$_n$, (LARL)$_n$, HA2; RGD; K$_1$ 6RGD, oligomer; AlkCWK$_{18}$, DiCWK18, DipaLytic; Plae, Kplae and other delivery agents known in the art or developed in the future.

A delivery agent useful in the present invention also can be an agent that enables or enhances cellular uptake of the domains of the composition of the present invention that are associated non-covalently. In one embodiment, such a delivery agent is peptide containing two independent domains: a hydrophobic domain and a hydrophilic domain. In another embodiment, such a delivery agent is an MPG peptide, which is a peptide derived from both the nuclear localization sequence (NLS) of SV40 large T antigen and the fusion peptide domain of HIV-1 gP$_{41}$. In a further embodiment, such a delivery agent is an MPG peptide having the amino acid sequence GALFLGFLGAAGSTMGAWSQPKSKRKV (SEQ ID NO:27). In yet a further embodiment, such a delivery agent is an amphipathic peptide such as Pep-1. These and related delivery agents that function in the absence of covalent linkage, also referred to as "protein transfection products," can be used as the delivery system or the "TCB" domain of the present invention. Such peptide delivery agents/TCB domains for use with the composition of the present invention can be prepared by methods known in the art and/or are commercially available; as an example, the Chariot™ product is available from Active Motif (Carlsbad, Calif.).

Methods of Inhibiting a Toxin

The present invention relates to inhibiting one or more toxins, toxin active fragments, or toxin serotypes by contacting the composition of the present invention with the toxin. In particular, these methods are applicable in vitro and in vivo.

In vivo, the composition of the present invention is contacted with a cell intoxicated with the toxin active fragment that is the target of the toxin binding domain of the composition. The cell can be intoxicated using methods known in the art. For example, the cell can be intoxicated if the toxin is the holotoxin, or has the enzymatically active portion of the toxin fused with a cell binding/translocation domain. For example, the light chain of the BoNT/A can be delivered to a cell in any number of ways known in the art, and include exposing the enzymatically active portion of the toxin to the cell in concentrations and subjecting the mixture to conditions that allow entry of the toxin active fragment into the cell.

After the cell is intoxicated with the toxin active fragment or toxin, the intoxicated cell is exposed to or comes into contact with the composition of the present invention. The toxin-binding domain binds the toxin active fragment and the E3 ubiquitin ligase domain facilitates polyubiquitination and the subsequent degradation of the toxin. The composition of the present invention is exposed to the intoxicated cell in an amount ranging from about 1 nM to about 100 mM, and for a length of time ranging from about 1 minute and about 1 week.

In vivo, the composition of the present invention is administered to an individual exposed to the toxin. The toxin enters cells of the individual and often causes paralysis or other symptoms depending on the type of toxin. The present invention includes methods of administering one or more designer ubiquitin ligases, described herein, to an individual. The toxin binding domain binds to the toxin active fragment that has intoxicated the cells of the individual. The amount of recombinant ubiquitin ligase of the present invention can be administered to the individual ranges from about 100 ng to about 5 gm.

In one aspect, the present invention embodies targeting multiple toxins or toxin serotypes. This can be accomplished at least in two ways using the compositions of the present invention. The composition of the present invention can include more than one toxin binding domains, each specific to a different portion of the same toxin active fragment or to different toxin active fragments of different toxins. In another embodiment, multiple designer ubiquitin ligases, each to target different areas of one or more toxins are administered. In an embodiment, two, three or more different enzymatically active portions of a toxin or toxin serotypes (e.g., BoNT serotype A, B, C, etc.), can be used as the target for the toxin binding domain. In a case in which a number of serotypes can be involved in causing a disease or condition, such as botulism, multiple enzymatic portions of the toxin serotypes can be targeted. In the case of botulism, since any one of at least seven neurotoxin serotypes could be responsible for botulism, a molecule having with toxin binding domain to one, all, or any combination of the BoNT serotypes is encompassed by the present invention. Alternatively, a pool of designer ligases can be prepared that contain an toxin binding domain that is specific for the enzymatic portion of one or more known serotypes that cause human disease. Botulism is often caused by exposure to a single BoNT serotype, but it is generally difficult to quickly determine which serotype is the cause. Thus, the standard of care in treating botulism includes administration of a number of antibodies to protect against most if not all of the serotypes that cause the disease in human. Hence, to protect against such a disease, an embodiment of the present invention includes having a cocktail of more than one designer ligase so that the ligases bind to several or preferably all of the serotypes that cause botulism. In such a case, the E3-ligase domain, as further described herein, can remain constant among the various designer ligases, whereas in another embodiment, they can differ.

The methods of the present invention include treating an individual infected with one or more toxins. This is accomplished by administering the designer ubiquitin ligase of the present invention to the infected individual. Administration ameliorates or reduces the severity of one or more the symptoms of the disease or condition. The presence, absence, or severity of symptoms can be measured using tests and diagnostic procedures known in the art. Similarly the presence, absence and/or level of the toxin can be measured using methods known in the art. Symptoms or levels of the toxin can be measured at one or more time points (e.g., before, during and after treatment, or any combination thereof) during the course of treatment to determine if the treatment is effective. A decrease or no change in the level of the disease agent, or severity of symptoms associated therewith indicates that treatment is working, and an increase in the level of the toxin, or severity of symptoms indicates that treatment is not working. Symptoms and levels of toxin are measured using methods known in the art.

In another embodiment, a formulation of the present invention can contain one or more of the DNA molecules that encode the designer ubiquitin ligase or portion thereof either present as a mixture or in the form of a DNA fusion molecule, each DNA molecule encoding a polypeptide as described above, such that the polypeptide is generated in situ. The DNA of the present invention can be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). In a preferred embodiment, the DNA can be introduced using a viral expression system (e.g., vaccinia or other pox virus, retrovirus, lentivirus, adenovirus, and adeno-associated virus), which can involve the use of a non-pathogenic (defective), replication competent virus. In particular, adeno-associated viral delivery can be used to deliver nucleic acid molecules that encode the designer ubiquitin of the present invention. Techniques for incorporating DNA into such expression systems are well known to those of ordinary skill in the art. The DNA can also be "naked," as described, for example, in Ulmer et al., Science 259:1745-1749, 1993 and reviewed by Cohen, Science 259:1691-1692, 1993. The uptake of naked DNA can be increased by coating the DNA onto biodegradable beads, which are efficiently transported into the cells.

The designer ubiquitin ligase of the present invention can be administered in one or more pharmaceutical carriers. The terms "pharmaceutically acceptable carrier" or a "carrier" refer to any generally acceptable excipient or drug delivery device that is relatively inert and non-toxic. The designer ubiquitin ligase of the present invention can be administered with or without a carrier. Exemplary carriers include calcium carbonate, sucrose, dextrose, mannose, albumin, starch, cellulose, silica gel, polyethylene glycol (PEG), dried skim milk, rice flour, magnesium stearate, and the like. Suitable formulations and additional carriers are described in Remington's Pharmaceutical Sciences, (17th Ed., Mack Pub. Co., Easton, Pa.), the teachings of which are incorporated herein by reference in their entirety. The ubiquitin designer ligase of the present invention can be administered systemically or locally (e.g., by injection or diffusion).

Suitable carriers (e.g., pharmaceutical carriers) also include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. Such preparations can be sterilized and, if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation. A carrier (e.g., a pharmaceutically acceptable carrier) is preferred, but not necessary to administer one or more designer ubiquitin ligases.

The designer ubiquitin ligase of the present invention can be administered intravenously, parenterally, orally, nasally, by inhalation, by implant, by injection, or by suppository. The composition can be administered in a single dose or in more than one dose over a period of time to confer the desired effect.

The actual effective amounts of compositions of the present invention can vary according to the designer ubiquitin ligase being utilized, the particular composition formulated, the mode of administration and the age, weight and condition of the patient, for example. As used herein, an effective amount of the designer ubiquitin ligase of the present invention is an amount which is capable of reducing one or more symptoms of the disease or conditions caused by the toxin. Dosages for a particular patient can be determined by one of ordinary skill in the art using conventional considerations, (e.g. by means of an appropriate, conventional pharmacological protocol).

The administration of the composition of the present invention and other anti-toxin drugs can occur simultaneously or sequentially in time to confer the desired effect.

Systems or kits of the present invention include one or more designer ubiquitin ligase of the present invention, as described herein.

Polypeptides, Nucleic Acid Sequences, Vectors, Host Cells of Designer Ubiquitin Ligase of the Present Invention As used herein, the term "recombinant" refers to a molecule that is one that is genetically made using techniques described herein. The present invention relates to a "recombinant" ubiquitin ligase or portions thereof that are engineered genetically. The present invention also pertains to polypeptide molecules that are encoded by nucleic acid sequences, SEQ ID NO: 5, 9, 11, 13, or combinations thereof).

As used herein, the term "polypeptide" encompasses amino acid chains of the designer ubiquitin ligase having any length, partial or full length proteins, wherein the amino acid residues are linked by covalent peptide bonds. Thus, a polypeptide can comprise a portion of the designer ubiquitin ligase or domain thereof, or it can contain additional sequences. Note that terms, "heavy chain" and "light chain", can be used describe a portion of the antibody fragment being used, but also can refer to the domain of the toxin (e.g., the light chain is the enzymatically active portion, and the heavy chain is the translocation/cell binding domain), depending on the context the term is being used.

Specifically, the present invention relates to recombinant designer ubiquitin ligases having a toxin binding domain such as the non-cleavable SNAP25 domain (SEQ ID NO: 6) and an E3 ligase domain such as the RING domain (SEQ ID NO: 10). Similarly, the present invention also includes a composition that is encoded by a nucleic acid sequence of SEQ ID NO: 5 and 9.

The polypeptides of the present invention referred to herein as "isolated" are polypeptides that are separated away from other proteins and cellular material of their source of origin. The compositions and methods of the present invention also encompass variants of polypeptides and DNA molecules of the present invention. A polypeptide "variant," as used herein, is a polypeptide that differs from the recited polypeptide only in conservative substitutions and/or modifications, such that the ability of the designer ubiquitin ligase is retained.

The present invention also encompasses proteins and polypeptides, variants thereof, or those having amino acid sequences analogous to the amino acid sequences of binding agents described herein. Such polypeptides are defined herein as analogs (e.g., homologues), or mutants or derivatives. "Analogous" or "homologous" amino acid sequences refer to amino acid sequences with sufficient identity of any one of the amino acid sequences of the present invention so as to possess the biological activity (e.g., the ability to bind to the toxin). For example, an analog polypeptide can be produced with "silent" changes in the amino acid sequence wherein one, or more, amino acid residues differ from the amino acid residues of any one of the sequence, yet still possesses the function or biological activity of the polypeptide. In particular, the present invention relates to homologous polypeptide molecules having at least about 70% (e.g., 75%, 80%, 85%, 90% or 95%) identity or similarity with SEQ ID NO: 6, 10, 12, 14, or combination thereof. Percent "identity" refers to the amount of identical nucleotides or amino acids between two nucleotides or amino acid sequences, respectfully. As used herein, "percent similarity" refers to the amount of similar or conservative amino acids between two amino acid sequences.

Homologous polypeptides can be determined using methods known to those of skill in the art. Initial homology searches can be performed at NCBI against the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the Find-Patterns subroutines of the Genetics Computing Group (GCG, version 8.0) software. Protein and/or nucleotide comparisons were performed according to Higgins and Sharp (Higgins, D. G. and Sharp, P. M., Gene, 73:237-244 (1988) e.g., using default parameters).

The present invention, in one embodiment, includes an isolated nucleic acid molecule having a sequence of SEQ ID NO: 5, 9, 11, 13, or combinations thereof. See FIGS. 8A-D. As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, truncations, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

As used herein, an "isolated" nucleotide sequence is a sequence that is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences that encode the toxin binding domain of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the toxin binding domains described herein. In particular, the present invention is directed to nucleic acid molecules having at least about 70% (e.g., 75%, 80%, 85%, 90% or 95%) identity with SEQ ID NO: SEQ ID NO: 5, 9, 11, 13, or combinations thereof.

Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleic acid need not reflect the exact sequence of the sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

Stringency Conditions for Nucleic Acids:

Specific hybridization can be detected under high stringency conditions. "Stringency conditions" for hybridization is a term of art which refers to the conditions of temperature and buffer concentration which permit and maintain hybridization of a particular nucleic acid to a second nucleic acid; the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" for nucleic acid hybridizations and subsequent washes are explained, e.g., on pages 2.10.1-2.10.16 and pages 6.3.1-6 in Current Protocols in Molecular Biology (Ausubel, et al., In: Current Protocols in Molecular Biology, John Wiley & Sons, (1998)). The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined. Exemplary conditions are described in the art (Krause, M. H., et al., 1991, Methods Enzymol. 200:546-556). Also, low and moderate stringency conditions for washes are described (Ausubel, et al., In: Current Protocols in Molecular Biology, John Wiley & Sons, (1998)). Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in Tm of about 17° C. Using these guidelines, the washing temperature can be determined empirically for high stringency, depending on the level of the mismatch sought. In some embodiments, high stringency conditions include those in which nucleic acid with less than a few mismatches does not bind. High stringency conditions, using these guidelines, lie in a temperature range between about 40° C. and about 60° C., an SSC concentration range between about 1× and about 10× (e.g., about 2×), and a reaction time range of between about 30 seconds and about 36 hours.

The present invention also provides vectors, plasmids or viruses containing one or more of the nucleic acid molecules having the sequence of SEQ ID NO: SEQ ID NO: 5, 9, 11, 13, or combinations thereof). Suitable vectors for use in eukaryotic and prokaryotic cells are known in the art and are commercially available or readily prepared by a skilled artisan. Additional vectors can also be found, for example, in Ausubel, F. M., et al., Current Protocols in Molecular Biology, (Current Protocol, 1994) and Sambrook et al., "Molecular Cloning: A Laboratory Manual," 2nd ED. (1989).

Peptidomimetic

Any polypeptide, or domain and/or portion thereof, described herein, can be substituted with a peptidomimetic. As used herein, the term "peptidomimetic" is used broadly to mean a peptide-like molecule that functions in the same manner as the polypeptides of the present invention. Such peptidomimetics include chemically modified peptides, peptide-like molecules containing non-naturally occurring amino acids, and peptoids, which are peptide-like molecules resulting from oligomeric assembly of N-substituted glycines, and function in a similar way as the toxin active fragment upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

A variety of peptidomimetics are known in the art including, for example, peptide-like molecules which contain a constrained amino acid, a non-peptide component that mimics peptide secondary structure, or an amide bond isostere. A peptidomimetic that contains a constrained, non-naturally occurring amino acid can include, for example, an α-methylated amino acid; an α,α-dialkyl-glycine or α-aminocycloalkane carboxylic acid; an $N^\alpha$-$C^\alpha$ cyclized amino acid; an $N^\alpha$-methylated amino acid; a β- or γ-amino cycloalkane carboxylic acid; an α,β-unsaturated amino acid; a β,β-dimethyl or β-methyl amino acid; a β-substituted-2,3-methano amino acid; an $NC^\Delta$ or $C^\alpha$-$C^\alpha$ cyclized amino acid; or a substituted proline or another amino acid mimetic. In addition, a peptidomimetic which mimics peptide secondary structure can contain, for example, a nonpeptidic β-turn mimic; γ-turn mimic; mimic of β-sheet structure; or mimic of helical structure, each of which is well known in the art. A peptidomimetic also can be a peptide-like molecule which contains, for example, an amide bond isostere such as a retro-inverso modification; reduced amide bond; methylenethioether or methylenesulfoxide bond; methylene ether bond; ethylene bond; thioamide bond; trans-olefin or fluoroolefin bond; 1,5-disubstituted tetrazole ring; ketomethylene or fluoroketomethylene bond or another amide isostere. One skilled in the art understands that these and other peptidomimetics are encompassed within the meaning of the term "peptidomimetic" as used herein.

Exemplification

In FIG. 6A, the increased ubiquitination of BoNT/A LC by the SNAP25/NC-RING designer ubiquitin ligase is demonstrated by the increase amount of a anti-ubiquitin immunoreactivity in samples that have been transfected with the BoNT/A LC. In FIG. 6B, the decrease in steady state levels of BoNT/A LC protein in samples transfected with SNAP25/NC-RING ubiquitin ligase. In combination the results of these two figures demonstrate that in the presence of SNAP25/NC-RING designer ubiquitin ligase, increased amount of ubiquitination of BoNT/A LC is induced and the steady state amount of BoNT/A LC is decreased. In the presence of SNAP25/NC-RING, this decrease in BoNT/A LC is due to this increased ubiquitination and proteasome degradation (See in FIG. 7). To accomplish the experiments shown in FIG. 6A, N2a cells were cotransfected expression plasmids encoding YFP-BoNT/A LC and either SNAP25/NC control expressing plasmid or SNAP25/NC-RING expressing plasmid. The N2a cells were lysed 24 hours after transfection and the YFP-BoNT/A LC was immunoprecipitated using anti-GFP antibody, which also recognizes YFP tags. The immunoprecipitated YFP-BoNT/A LC from both the SNAP25/NC control and SNAP25/NC-RING samples was analyzed by SDS-PAGE followed by immunobloting for either YFP-BoNT/A LC or ubiquitin. The panel probed with antibody for YFP demonstrates essentially equal amounts of YFP-BoNT/A LC were immunoprecipitated. In the panel showing a blot probed with anti-ubiquitin antibody demonstrates significantly more anti-ubiquitin immunoreactivity of the immunoprecipitated YFP-BoNT/A LC sample co-transfected with the SNAP25/NC-RING compared to the SNAP25/NC control transfection. The anti-ubiquitin immunoreactivity is present in a high molecular weight smearing pattern characteristic of ubiquitination.

In FIG. 6B, N2a samples were contransfected with YFP-BoNT/A LC and either SNAP25/NC control or SNAP25/NC-RING plasmid. The N2a cells were lysed 24 hours after transfection and analyzed by SDS-PAGE followed by immunobloting with anti-GFP antibody to demonstrate the steady state level of YFP-BoNT/A LC. The amount of YFP-BoNT/A on the immunoblot is much lower in the samples cotransfected with SNAP25/NC-RING designer ubiquitin ligase than in the SNAP25/NC control sample.

To determine the effect of the SNAP25/NC-RING designer ubiquitin ligase on the rate of degradation of the YFP-BoNT/A LC, N18 neuroblastoma cells were transfected with YFP-BoNT/A LC alone, YFP-BoNT/A LC with SNAP25/NC, YFP-BoNT/A LC with SNAP25/NC-RING. The cells were treated by radiolabeling with 35S-methionine for 60 minutes followed by chase for various periods of time using standard pulse-chase procedures 24 hours after transfection. The cells were harvested, lysed and the radiolabeled YFP-BoNT/A LC immunoprecipitated with anti-GFP antibody. The immunoprecipitated YFP-BoNT/A LC was then assessed by autoradiography and the amount of radiolabel in the YFP-BoNT/A LC determined. The rate of degradation of the YFP-BoNT/A LC was determined by graphing amount of radiolabeled YFP-BoNT/A LC vs chase time as shown in FIG. 7. Assessment of FIG. 7 demonstrates co-transfection of YFP-BoNT/A LC with SNAP25/NC control has no effect on the rate of YFP-BoNT/A LC decay compared to the sample of YFP-BoNT/A LC alone. The sample of YFP-BoNT/A LC cotransfected with SNAP25/NC-RING designer ligase has much more rapid degradation of YFP-BoNT/A LC. This results suggests that the SNAP25/NC-RING designer ligase is capable of accelerating YFP-BoNT/A LC degradation. To determine if the mechanism of this accelerated degradation is due to the a ubiquitin proteasome mediated mechanism, the proteasome was inhibited with MG132. In the presence of MG132 inhibition of the proteasome, the cotransfection of SNAP25/NC-RING is no longer able to accelerate the degradation of YFP-BoNT/A LC.

Taking the results illustrated in FIG. 6A-6B and 7 together the SNAP25/NC-RING designer ubiquitin ligase has been demonstrated to increase the ubiquitination of BoNT/A LC, to decrease both the steady state level of the BoNT/A LC and to accelerate the rate of degradation by pulse chase analysis. The acceleration of BoNT/A LC degradation by SNAP25/NC-RING designer ubiquitin ligase has been shown to be dependent on proteasome activity. These experiments represent proof of concept that a designer ubiquitin ligase formed from a domain with affinity for the BoNT/A LC (the SNAP25/NC domain) and an E3 domain (RING domain) is able to accelerate the ubiquitination and proteasome degradation of a BoNT/A LC toxin enzymatically active domain in cells. The ability of such a designer ubiquitin ligase to accelerate the degradation of the toxin active fragment represents the demonstration of the basis for a cellular therapeutic approach to treatment of intoxication.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. An isolated recombinant ubiquitin ligase molecule that comprises:
   a. a toxin binding domain that has an affinity for an enzymatically active fragment of one or more toxins or toxin serotypes, wherein the toxin binding domain comprises a non-cleavable SNAP-25 domain that is encoded by a nucleic acid molecule that consists essentially of a nucleic acid sequence selected from the group consisting of:
      i. a nucleic acid sequence having greater than or equal to about 90% identity with nucleic acid bases 1 to 618 of SEQ ID NO: 11 or 13;
      ii. a nucleic acid sequence complement having greater than or equal to about 90% identity with nucleic acid bases 1 to 618 of SEQ ID NO: 11 or 13;
      iii. a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. a nucleic acid sequence that encodes an amino acid sequence having greater than or equal to about 90% similarity to a sequence set forth in amino acid bases 1 to 206 of SEQ ID NO: 12 or 14; and
   b. an E3-ligase domain that comprises an E3-ligase or polypeptide that facilitates E2-mediated ubiquitination of the toxin enzymatically active fragment, wherein the E3-ligase domain is encoded by a nucleic acid molecule that consists essentially of a nucleic acid sequence selected from the group consisting of:
      i. a nucleic acid sequence having greater than or equal to about 90% identity with nucleic acid bases from 619 to 1029 of SEQ ID NO: 11 or 13;
      ii. a nucleic acid sequence complement having greater than or equal to about 90% identity with nucleic acid bases from 619 to 1029 of SEQ ID NO: 11 or 13;
      iii. a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. a nucleic acid sequence that encodes an amino acid sequence having greater than or equal to about 90% similarity to a sequence set forth in amino acid bases 207 to 343 of SEQ ID NO: 12 or 14.

2. The isolated recombinant ubiquitin ligase molecule of claim 1, wherein the non-cleavable SNAP-25 domain binds to the enzymatically active fragment of a botulinum neurotoxin (BoNT).

3. An isolated recombinant ubiquitin ligase molecule that comprises:
   a. a toxin binding domain that has an affinity for an enzymatically active fragment of one or more toxins or toxin serotypes, wherein the toxin binding domain comprises a non-cleavable SNAP-25 domain, wherein the non-cleavable SNAP-25 domain consists essentially of an amino acid sequence selected from the group consisting of:
      i. an amino acid sequence encoded by a nucleic acid having greater than or equal to about 90% identity with nucleic acid bases 1 to 618 of SEQ ID NO: 11 or 13;
      ii. an amino acid sequence encoded by a complement having greater than or equal to about 90% identity with of nucleic acid bases 1 to 618 of SEQ ID NO: 11 or 13;
      iii. an amino acid sequence encoded by a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. an amino acid sequence having greater than or equal to about 90% similarity to a sequence set forth in amino acid bases 1 to 206 of SEQ ID NO: 12 or 14; and
   b. an E3-ligase domain that comprises an E3-ligase or polypeptide that facilitates E2-mediated ubiquitination of the toxin enzymatically active fragment, wherein the E3-ligase domain consists essentially of an amino acid sequence selected from the group consisting of:
      i. an amino acid sequence encoded by a nucleic acid having greater than or equal to about 90% identity with nucleic acid bases from 619 to 1029 of SEQ ID NO: 11 or 13;
      ii. an amino acid sequence encoded by a complement having greater than or equal to about 90% identity with nucleic acid bases from 619 to 1029 of SEQ ID NO: 11 or 13;
      iii. an amino acid sequence encoded by a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. an amino acid sequence having greater than or equal to about 90% similarity to a sequence set forth in amino acid bases 207 to 343 of SEQ ID NO: 12 or 14.

4. The isolated recombinant ubiquitin ligase molecule of claim 2, wherein the serotypes comprise BoNT serotypes A, C, or E.

5. An isolated recombinant ubiquitin ligase molecule that is encoded by a nucleic acid molecule that consists essentially of a nucleic acid sequence selected from the group consisting of:
   a. a nucleic acid sequence having greater than or equal to about 90% identity with SEQ ID NO: 11 or 13;
   b. a nucleic acid sequence complement having greater than or equal to about 90% identity with of SEQ ID NO: 11 or 13;
   c. a nucleic acid molecule that hybridizes to SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
   d. a nucleic acid sequence that encodes an amino acid sequence having greater than or equal to about 90% similarity to a sequence set forth in SEQ ID NO: 12 or 14 wherein the isolated recombinant ubiquitin ligase molecule comprises a non-cleavable SNAP-25 toxin binding domain that binds to the enzymatically active fragment of BoNT, and a RING E3-ligase domain that facilitates E2-mediated ubiquitination of the toxin enzymatically active fragment.

6. An isolated recombinant ubiquitin ligase molecule that consists essentially of an amino acid sequence selected from the group consisting of:
   a. an amino acid sequence encoded by a nucleic acid having greater than or equal to about 90% identity with SEQ ID NO: 11 or 13;
   b. an amino acid sequence encoded by a complement having greater than or equal to about 90% identity with of SEQ ID NO: 11 or 13;
   c. an amino acid sequence encoded by a nucleic acid that hybridizes to SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
   d. an amino acid sequence having greater than or equal to about 90% similarity to a sequence set forth in SEQ ID NO: 12 or 14
wherein the isolated recombinant ubiquitin ligase molecule comprises a non-cleavable SNAP-25 toxin binding domain that binds to the enzymatically active fragment of BoNT, and a RING E3-ligase domain that facilitates E2-mediated ubiquitination of the toxin enzymatically active fragment.

7. An isolated polypeptide molecule that comprises:
   a. a non-cleavable SNAP-25 domain that has affinity to the enzymatically active fragment of a BoNT, wherein the non-cleavable SNAP-25 domain is encoded by a nucleic acid molecule that consists essentially of a nucleic acid sequence selected from the group consisting of:
      i. a nucleic acid sequence having greater than or equal to about 90% identity with nucleic acid bases 1 to 618 of SEQ ID NO: 11 or 13;
      ii. a nucleic acid sequence complement having greater than or equal to about 90% identity with nucleic acid bases 1 to 618 of SEQ ID NO: 11 or 13;
      iii. a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. a nucleic acid sequence that encodes an amino acid sequence having greater than or equal to about 90% similarity to a sequence set forth in amino acid bases 1 to 206 of SEQ ID NO: 12 or 14;
   b. a BoNT holotoxin, wherein the BoNT holotoxin comprises a deletion in the light chain, a mutation of the heavy chain, or both, wherein the deletion, mutation or both renders BoNT holotoxin atoxic; and
   c. an E3-ligase domain that comprises an E3-ligase or polypeptide that facilitates E2-mediated degradation of the toxin enzymatically active fragment of a BoNT; wherein the E3-ligase domain is encoded by a nucleic acid molecule that consists essentially of a nucleic acid sequence selected from the group consisting of:
      i. a nucleic acid sequence having greater than or equal to about 90% identity with nucleic acid bases from 619 to 1029 of SEQ ID NO: 11 or 13;
      ii. a nucleic acid sequence complement having greater than or equal to about 90% identity with nucleic acid bases from 619 to 1029 of SEQ ID NO: 11 or 13;
      iii. a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. a nucleic acid sequence that encodes an amino acid sequence having greater than or equal to about 90% similarity to a sequence set forth in amino acid bases 207 to 343 of SEQ ID NO: 12 or 14;
   wherein non-cleavable SNAP-25 domain and the BoNT atoxic holotoxin are fused.

8. The isolated polypeptide molecule of claim 7, wherein the non-cleavable SNAP-25 domain is fused to the N-terminus of the BoNT atoxic holotoxin.

9. A fusion protein comprising the isolated polypeptide of claim 7.

10. An isolated recombinant ubiquitin ligase molecule that comprises:
   a. a non-cleavable SNAP-25 domain that has affinity to the enzymatically active fragment of a BoNT, wherein the non-cleavable SNAP-25 domain is encoded by a nucleic acid molecule that consists essentially of a nucleic acid sequence selected from the group consisting of:
      i. a nucleic acid sequence having greater than or equal to about 90% identity with nucleic acid bases 1 to 618 of SEQ ID NO: 11 or 13;
      ii. a nucleic acid sequence complement having greater than or equal to about 90% identity with nucleic acid bases 1 to 618 of SEQ ID NO: 11 or 13;
      iii. a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. a nucleic acid sequence that encodes an amino acid sequence having greater than or equal to about 90% similarity to a sequence set forth in amino acid bases 1 to 206 of SEQ ID NO: 12 or 14;
   b. an E3-ligase domain that comprises an E3-ligase or polypeptide that facilitates E2-mediated ubiquitination of the toxin enzymatically active fragment, wherein the E3-ligase domain is encoded by a nucleic acid molecule that consists essentially of a nucleic acid sequence selected from the group consisting of:
      i. a nucleic acid sequence having greater than or equal to about 90% identity with nucleic acid bases from 619 to 1029 of SEQ ID NO: 11 or 13;
      ii. a nucleic acid sequence complement having greater than or equal to about 90% identity with nucleic acid bases from 619 to 1029 of SEQ ID NO: 11 or 13;
      iii. a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and iv. a nucleic acid sequence that encodes an amino acid sequence having greater than or equal to about 90% similarity to a sequence set forth in amino acid bases 207 to 343 of SEQ ID NO: 12 or 14; and c. a translocation cellular binding domain or to the N-terminus of the BoNT atoxic holotoxin.

11. The isolated recombinant ubiquitin ligase molecule of claim 10, wherein the translocation cellular binding domain binds to the cellular membrane of a cell and delivers the recombinant ubiquitin ligase into the cell.

12. An isolated recombinant ubiquitin ligase molecule that comprises:
   a. a non-cleavable SNAP-25 domain that binds to the enzymatically active fragment of a BoNT, wherein the non-cleavable SNAP-25 domain is encoded by a nucleic acid molecule that comprises a nucleic acid sequence selected from the group consisting of:
      i. a nucleic acid sequence having nucleic acid bases 1 to 618 of SEQ ID NO: 11;
      ii. a nucleic acid sequence complement of nucleic acid bases 1 to 618 of SEQ ID NO: 11;
      iii. a nucleic acid molecule that hybridizes to nucleic acid bases 1 to 618 of SEQ ID NO: 11 under high stringency conditions, wherein said conditions comprise a temperature range between about 40° C. and about 60° C., an SSC concentration range between about 1× and about 10× and a reaction time range of between about 30 seconds and about 36 hours; and
      iv. a nucleic acid sequence that encodes an amino acid sequence having a sequence set forth in amino acid bases 1 to 206 of SEQ ID NO: 12; and
   b. an E3-ligase domain that comprises an E3-ligase or polypeptide that facilitates E2-mediated ubiquitination of the toxin enzymatically active fragment.

13. The isolated recombinant ubiquitin ligase molecule of claim 12, wherein the E3-ligase domain comprises a RING domain encoded by a nucleic acid molecule that comprises a nucleic acid sequence selected from the group consisting of:
   i. a nucleic acid sequence having nucleic acid bases from 619 to 1029 of SEQ ID NO: 11 or 13;
   ii. a nucleic acid sequence complement of nucleic acid bases from 619 to 1029 of SEQ ID NO: 11 or 13;
   iii. a nucleic acid molecule with a molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
   iv. a nucleic acid sequence that encodes an amino acid sequence set forth in amino acid bases 207 to 343 of SEQ ID NO: 12 or 14.

14. An isolated recombinant ubiquitin ligase molecule that comprises:
   a. a non-cleavable SNAP-25 domain that binds to the enzymatically active fragment of a BoNT, wherein the non-cleavable SNAP-25 domain that comprises an amino acid sequence selected from the group consisting of:
      i. an amino acid sequence encoded by a nucleic acid having nucleic acid bases 1 to 618 of SEQ ID NO: 11 or 13;
      ii. an amino acid sequence encoded by a complement nucleic acid bases 1 to 618 of SEQ ID NO: 11 or 13;
      iii. an amino acid sequence encoded by a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. an amino acid sequence having a sequence set forth in amino acid bases 1 to 206 of SEQ ID NO: 12 or 14; and
   b. an E3-ligase domain that comprises an E3-ligase or polypeptide that facilitates E2-mediated ubiquitination of the toxin enzymatically active fragment.

15. The isolated recombinant ubiquitin ligase molecule of claim 14, wherein the E3-ligase domain comprises a RING domain that comprises an amino acid sequence selected from the group consisting of:
   i. an amino acid sequence encoded by a nucleic acid having nucleic acid bases from 619 to 1029 of SEQ ID NO: 11 or 13;
   ii. an amino acid sequence encoded by a complement of nucleic acid bases from 619 to 1029 of SEQ ID NO: 11 or 13;
   iii. an amino acid sequence encoded by a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
   iv. an amino acid sequence set forth in amino acid bases 207 to 343 of SEQ ID NO: 12 or 14.

16. An isolated polypeptide molecule that comprises:
   a. a non-cleavable SNAP-25 domain that has affinity to the enzymatically active fragment of a BoNT, wherein the non-cleavable SNAP-25 domain consists essentially of an amino acid sequence selected from the group consisting of:
      i. an amino acid sequence encoded by a nucleic acid having greater than or equal to about 90% identity with nucleic acid bases 1 to 618 of SEQ ID NO: 11 or 13;
      ii. an amino acid sequence encoded by a complement having greater than or equal to about 90% identity with of nucleic acid bases 1 to 618 of SEQ ID NO: 11 or 13;
      iii. an amino acid sequence encoded by a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. an amino acid sequence having greater than or equal to about 90% similarity to a sequence set forth in amino acid bases 1 to 206 of SEQ ID NO: 12 or 14;
   b. a BoNT holotoxin, wherein the BoNT holotoxin comprises a deletion in the light chain, a mutation of the heavy chain, or both, wherein the deletion, mutation or both renders BoNT holotoxin atoxic; and
   c. an E3-ligase domain that comprises an E3-ligase or polypeptide that facilitates E2-mediated degradation of the toxin enzymatically active fragment of a BoNT;

wherein E3-ligase domain comprises an amino acid sequence selected from the group consisting of:
  i. an amino acid sequence encoded by a nucleic acid having greater than or equal to about 90% identity with nucleic acid bases from 619 to 1029 of SEQ ID NO: 11 or 13;
  ii. an amino acid sequence encoded by a complement having greater than or equal to about 90% identity with nucleic acid bases from 619 to 1029 of SEQ ID NO: 11 or 13;
  iii. an amino acid sequence encoded by a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
  iv. an amino acid sequence having greater than or equal to about 90% similarity to a sequence set forth in amino acid bases 207 to 343 of SEQ ID NO: 12 or 14;
wherein non-cleavable SNAP-25 domain and the BoNT atoxic holotoxin are fused.

17. The isolated polypeptide molecule of claim 16, wherein the non-cleavable SNAP-25 domain is fused to the N-terminus of the BoNT atoxic holotoxin.

18. A fusion protein comprising the isolated polypeptide of claim 16.

19. An isolated recombinant ubiquitin ligase molecule that comprises:
  a. a non-cleavable SNAP-25 domain that has affinity to the enzymatically active fragment of a BoNT, wherein the non-cleavable SNAP-25 domain consists essentially of an amino acid sequence selected from the group consisting of:
    i. an amino acid sequence encoded by a nucleic acid having greater than or equal to about 90% identity with nucleic acid bases 1 to 618 of SEQ ID NO: 11 or 13;
    ii. an amino acid sequence encoded by a complement having greater than or equal to about 90% identity with of nucleic acid bases 1 to 618 of SEQ ID NO: 11 or 13;
    iii. an amino acid sequence encoded by a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
    iv. an amino acid sequence having greater than or equal to about 90% similarity to a sequence set forth in amino acid bases 1 to 206 of SEQ ID NO: 12 or 14;
  b. an E3-ligase domain that comprises an E3-ligase or polypeptide that facilitates E2-mediated ubiquitination of the toxin enzymatically active fragment, wherein E3-ligase domain comprises an amino acid sequence selected from the group consisting of:
    i. an amino acid sequence encoded by a nucleic acid having greater than or equal to about 90% identity with nucleic acid bases from 619 to 1029 of SEQ ID NO: 11 or 13;
    ii. an amino acid sequence encoded by a complement having greater than or equal to about 90% identity with nucleic acid bases from 619 to 1029 of SEQ ID NO: 11 or 13;
    iii. an amino acid sequence encoded by a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
    iv. an amino acid sequence having greater than or equal to about 90% similarity to a sequence set forth in amino acid bases 207 to 343 of SEQ ID NO: 12 or 14;
  c. a translocation cellular binding domain or to the N-terminus of the BoNT atoxic holotoxin.

20. The isolated recombinant ubiquitin ligase molecule of claim 19, wherein the translocation cellular binding domain binds to the cellular membrane of a cell and delivers the recombinant ubiquitin ligase into the cell.

21. An isolated recombinant ubiquitin ligase molecule that comprises:
  a. a non-cleavable SNAP-25 domain that binds to the enzymatically active fragment of a BoNT, wherein the non-cleavable SNAP-25 domain is encoded by a nucleic acid molecule that comprises a nucleic acid sequence selected from the group consisting of:
    i. a nucleic acid sequence having greater than or equal to about 90% identity with nucleic acid bases 1 to 618 of SEQ ID NO: 11 or 13;
    ii. a nucleic acid sequence complement having greater than or equal to about 90% identity with nucleic acid bases 1 to 618 of SEQ ID NO: 11 or 13;
    iii. a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
    iv. a nucleic acid sequence that encodes an amino acid sequence having greater than or equal to about 90% similarity to a sequence set forth in amino acid bases 1 to 206 of SEQ ID NO: 12 or 14; and
  b. an E3-ligase domain that comprises an E3-ligase or polypeptide that facilitates E2-mediated ubiquitination of the toxin enzymatically active fragment.

22. The isolated recombinant ubiquitin ligase molecule of claim 21, wherein the E3-ligase domain is encoded by a nucleic acid molecule that comprises a nucleic acid sequence selected from the group consisting of:
  i. a nucleic acid sequence having greater than or equal to about 90% identity with nucleic acid bases from 619 to 1029 of SEQ ID NO: 11 or 13;
  ii. a nucleic acid sequence complement having greater than or equal to about 90% identity with nucleic acid bases from 619 to 1029 of SEQ ID NO: 11 or 13;
  iii. a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
  iv. a nucleic acid sequence that encodes an amino acid sequence having greater than or equal to about 90% similarity to a sequence set forth in amino acid bases 207 to 343 of SEQ ID NO: 12 or 14.

23. An isolated recombinant ubiquitin ligase molecule that comprises:
   a. a non-cleavable SNAP-25 domain that binds to the enzymatically active fragment of a BoNT, wherein the non-cleavable SNAP-25 domain that comprises an amino acid sequence selected from the group consisting of:
      i. an amino acid sequence encoded by a nucleic acid having greater than or equal to about 90% identity with nucleic acid bases 1 to 618 of SEQ ID NO: 11 or 13;
      ii. an amino acid sequence encoded by a complement having greater than or equal to about 90% identity with of nucleic acid bases 1 to 618 of SEQ ID NO: 11 or 13;
      iii. an amino acid sequence encoded by a nucleic acid molecule that hybridizes to nucleic acid bases 1 to 618 of SEQ ID NO: 11 or 13 under high stringency conditions, wherein said conditions comprise a temperature range between about 40° C. and about 60° C., an SSC concentration range between about 1× and about 10× and a reaction time range of between about 30 seconds and about 36 hours; and
      iv. an amino acid sequence having greater than or equal to about 90% similarity to a sequence set forth in amino acid bases 1 to 206 of SEQ ID NO: 12 or 14; and
   b. an E3-ligase domain that comprises an E3-ligase or polypeptide that facilitates E2-mediated ubiquitination of the toxin enzymatically active fragment.

24. The isolated recombinant ubiquitin ligase molecule of claim 23, wherein the E3-ligase domain comprises an amino acid sequence selected from the group consisting of:
   i. an amino acid sequence encoded by a nucleic acid having greater than or equal to about 90% identity with nucleic acid bases from 619 to 1029 of SEQ ID NO: 11 or 13;
   ii. an amino acid sequence encoded by a complement having greater than or equal to about 90% identity with nucleic acid bases from 619 to 1029 of SEQ ID NO: 11 or 13;
   iii. an amino acid sequence encoded by a nucleic acid molecule that hybridizes to nucleic acid bases from 619 to 1029 of SEQ ID NO: 11 or 13 under high stringency conditions, wherein said conditions comprise a temperature range between about 40° C. and about 60° C., an SSC concentration range between about 1 and about 10× and a reaction time range of between about 30 seconds and about 36 hours; and
   iv. an amino acid sequence having greater than or equal to about 90% similarity to a sequence set forth in amino acid bases 207 to 343 of SEQ ID NO: 12 or 14.

* * * * *

SEQUENCE LISTING

<160> NUMBER OF SEQ ID NOS: 27

<210> SEQ ID NO 1
<211> LENGTH: 618
<212> TYPE: DNA
<213> ORGANISM: Homo sapiens

<400> SEQUENCE: 1

```
atggctgaag atgctgatat gcgtaatgaa cttgaagaaa tgcaacgtcg tgctgatcaa      60
cttgctgatg aatctcttga atctactcgt cgtatgcttc aacttgttga agaatctaaa     120
gatgctggta ttcgtactct tgttatgctt gatgaacaag gtgaacaact tgatcgtgtt     180
gaagaaggta tgaatcatat taatcaagat atgaaagaag ctgaaaaaaa tcttaaagat     240
cttggtaaat gttgtggtct ttttatttgt ccttgtaata aacttaaatc ttctgatgct     300
tataaaaaag cttggggtaa taatcaagat ggtgttgttg cttctcaacc tgctcgtgtt     360
gttgatgaac gtgaacaaat ggctatttct ggtggtttta ttcgtcgtgt tactaatgat     420
gctcgtgaaa atgaaatgga tgaaaatctt gaacaagttt ctggtattat tggtaatctt     480
cgtcatatgg ctcttgatat gggtaatgaa attgatactc aaaatcgtca aattgatcgt     540
attatggaaa aagctgattc taataaaact cgtattgatg aagctaatca acgtgctact     600
aaaatgcttg gttctggt                                                   618
```

<210> SEQ ID NO 2
<211> LENGTH: 206
<212> TYPE: PRT
<213> ORGANISM: Homo sapiens

<400> SEQUENCE: 2

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
            85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
            165                 170                 175

Gln Ile Asp Arg Ile Met Glu Lys Ala Asp Ser Asn Lys Thr Arg Ile
        180                 185                 190

Asp Glu Ala Asn Gln Arg Ala Thr Lys Met Leu Gly Ser Gly
        195                 200                 205

<210> SEQ ID NO 3
<211> LENGTH: 618
<212> TYPE: DNA
<213> ORGANISM: Homo sapiens

<400> SEQUENCE: 3
atggctgaag atgctgatat gcgtaatgaa cttgaagaaa tgcaacgtcg tgctgatcaa      60
cttgctgatg aatctcttga atctactcgt cgtatgcttc aacttgttga agaatctaaa     120
gatgctggta ttcgtactct tgttatgctt gatgaacaag gtgaacaact gaacgtatt      180 gaagaaggta tggatcaaat taataaagat atgaaagaag ctgaaaaaaa tcttactgat     240
cttggtaaat tttgtggtct ttgtgtttgt ccttgtaata aacttaaatc ttctgatgct     300
tataaaaaag cttgggggtaa taatcaagat ggtgttgttg cttctcaacc tgctcgtgtt     360
gttgatgaac gtgaacaaat ggctatttct ggtggtttta ttcgtcgtgt tactaatgat     420
gctcgtgaaa atgaaatgga tgaaaatctt gaacaagttt ctggtattat tggtaatctt     480
cgtcatatgg ctcttgatat gggtaatgaa attgatactc aaaatcgtca aattgatcgt     540
attatggaaa aagctgattc taataaaact cgtattgatg aagctaatca acgtgctact     600
aaaatgcttg gttctggt                                                   618

<210> SEQ ID NO 4
<211> LENGTH: 206
<212> TYPE: PRT
<213> ORGANISM: Homo sapiens

<400> SEQUENCE: 4

Met Ala Glu Asp Ala Asp Met Arg Asn Glu Leu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 5
<211> LENGTH: 147
<212> TYPE: DNA
<213> ORGANISM: artificial
<220> FEATURE:
<223> OTHER INFORMATION: synthetic construct

<400> SEQUENCE: 5
ggtaatcttc gtcatatggc tcttgatatg ggtaatgaaa ttgatactca aaatcgtcaa     60
attaaacgta ttatggaaaa agctgattct aataaaactc gtattgatga agctaatcaa    120
actgctacta aaatgcttgg ttctggt                                        147

<210> SEQ ID NO 6
<211> LENGTH: 49
<212> TYPE: PRT
<213> ORGANISM: artificial
<220> FEATURE:
<223> OTHER INFORMATION: synthetic construct

<400> SEQUENCE: 6

Gly Asn Leu Arg His Met Ala Leu Asp Met Gly Asn Glu Ile Asp Thr
1               5                   10                  15

Gln Asn Arg Gln Ile Lys Arg Ile Met Glu Lys Ala Asp Ser Asn Lys
            20                  25                  30

Thr Arg Ile Asp Glu Ala Asn Gln Thr Ala Thr Lys Met Leu Gly Ser
        35                  40                  45

Gly

<210> SEQ ID NO 7
<211> LENGTH: 1491
<212> TYPE: DNA

<213> ORGANISM: Unknown
<220> FEATURE:
<223> OTHER INFORMATION: baculovirus

<400> SEQUENCE: 7

```
atgacttta attcttttga aggttctaaa acttgtgttc ctgctgatat taataaagaa    60
gaagaatttg ttgaagaatt taatcgtctt aaaacttttg ctaattttcc ttctggttct   120
cctgttctg cttctactct tgctcgtgct ggttttcttt atactggtga aggtgatact   180
gttcgttgtt tttcttgtca tgctgctgtt gatcgttggc aatatggtga ttctgctgtt   240
ggtcgtcatc gtaaagtttc tcctaattgt cgttttatta tggttttta tcttgaaaat   300
tctgctactc aatctactaa ttctggtatt caaaatggtc aatataaagt tgaaaattat   360
cttggttctc gtgatcattt tgctcttgat cgtccttctg aaactcatgc tgattatctt   420
cttcgtactg gtcaagttgt tgatatttct gatactattt atcctcgtaa tcctgctatg   480
tattctgaag aagctcgtct taaatctttt caaaattggc ctgattatgc tcatcttact   540
cctcgtgaac ttgcttctgc tggtctttat tatactggta ttggtgatca agttcaatgt   600
ttttgttgtg gtgagtaaact taaaaattgg gaacctgtg atcgtgcttg gtctgaacat   660
cgtcgtcatt ttcctaattg tttttttgtt cttggtcgta atcttaatat tcgttctgaa   720
tctgatgctg tttcttctga tgtaattttt cctaattcta ctaatcttcc tcgtaatcct   780
tctatggctg attatgaagc tcgtattttt acttttggta cttggattta ttctgttaat   840
aaagaacaac ttgctcgtgc tggtttttat gctcttggtg aaggtgataa agttaaatgt   900
tttcattgtg gtggtggtct tactgattgg aaaccttctg aagatccttg ggaacaacat   960
gctaaatggt atcctggttg taaatatctt cttgaacaaa aaggtcaaga atatattaat  1020
aatattcatc ttactcattc tcttgaagaa tgtcttgttc gtactactga aaaaactcct  1080
tctcttactc gtcgtattga tgatactatt tttcaaaatc ctatggttca agaagctatt  1140
cgtatgggtt tttcttttaa agatattaaa aaaattatgg aagaaaaaat tcaaatttct  1200
ggttctaatt ataaatctct tgaagttctt gttgctgatc ttgttaatgc tcaaaaagat  1260
tctatgcaag atgaatcttc tcaaacttct cttcaaaaag aaatttctac tgaagaacaa  1320
cttcgtcgtc ttcaagaaga aaaactttgt aaaatttgta tggatcgtaa tattgctatt  1380
gttttttgttc cttgtggtca tcttgttact tgtaaacaat gtgctgaagc tgttgataaa  1440
tgtcctatgt gttatactgt tattacttt aaacaaaaaa ttttttatgtc t           1491
```

<210> SEQ ID NO 8
<211> LENGTH: 497
<212> TYPE: PRT
<213> ORGANISM: unknown
<220> FEATURE:
<223> OTHER INFORMATION: Baculovirus

<400> SEQUENCE: 8

```
Met Thr Phe Asn Ser Phe Glu Gly Ser Lys Thr Cys Val Pro Ala Asp
1               5                   10                  15

Ile Asn Lys Glu Glu Phe Val Glu Glu Phe Asn Arg Leu Lys Thr
            20                  25                  30

Phe Ala Asn Phe Pro Ser Gly Ser Pro Val Ser Ala Ser Thr Leu Ala
        35                  40                  45

Arg Ala Gly Phe Leu Tyr Thr Gly Glu Gly Asp Thr Val Arg Cys Phe
    50                  55                  60

Ser Cys His Ala Ala Val Asp Arg Trp Gln Tyr Gly Asp Ser Ala Val
65                  70                  75                  80
```

```
Gly Arg His Arg Lys Val Ser Pro Asn Cys Arg Phe Ile Asn Gly Phe
                85                  90                  95
Tyr Leu Glu Asn Ser Ala Thr Gln Ser Thr Asn Ser Gly Ile Gln Asn
            100                 105                 110
Gly Gln Tyr Lys Val Glu Asn Tyr Leu Gly Ser Arg Asp His Phe Ala
        115                 120                 125
Leu Asp Arg Pro Ser Glu Thr His Ala Asp Tyr Leu Leu Arg Thr Gly
    130                 135                 140
Gln Val Val Asp Ile Ser Asp Thr Ile Tyr Pro Arg Asn Pro Ala Met
145                 150                 155                 160
Tyr Ser Glu Glu Ala Arg Leu Lys Ser Phe Gln Asn Trp Pro Asp Tyr
                165                 170                 175
Ala His Leu Thr Pro Arg Glu Leu Ala Ser Ala Gly Leu Tyr Tyr Thr
            180                 185                 190
Gly Ile Gly Asp Gln Val Gln Cys Phe Cys Cys Gly Gly Lys Leu Lys
        195                 200                 205
Asn Trp Glu Pro Cys Asp Arg Ala Trp Ser Glu His Arg Arg His Phe
    210                 215                 220
Pro Asn Cys Phe Phe Val Leu Gly Arg Asn Leu Asn Ile Arg Ser Glu
225                 230                 235                 240
Ser Asp Ala Val Ser Ser Asp Arg Asn Phe Pro Asn Ser Thr Asn Leu
                245                 250                 255
Pro Arg Asn Pro Ser Met Ala Asp Tyr Glu Ala Arg Ile Phe Thr Phe
            260                 265                 270
Gly Thr Trp Ile Tyr Ser Val Asn Lys Glu Gln Leu Ala Arg Ala Gly
        275                 280                 285
Phe Tyr Ala Leu Gly Glu Gly Asp Lys Val Lys Cys Phe His Cys Gly
    290                 295                 300
Gly Gly Leu Thr Asp Trp Lys Pro Ser Glu Asp Pro Trp Glu Gln His
305                 310                 315                 320
Ala Lys Trp Tyr Pro Gly Cys Lys Tyr Leu Leu Glu Gln Lys Gly Gln
                325                 330                 335
Glu Tyr Ile Asn Asn Ile His Leu Thr His Ser Leu Glu Glu Cys Leu
            340                 345                 350
Val Arg Thr Thr Glu Lys Thr Pro Ser Leu Thr Arg Arg Ile Asp Asp
        355                 360                 365
Thr Ile Phe Gln Asn Pro Met Val Gln Glu Ala Ile Arg Met Gly Phe
    370                 375                 380
Ser Phe Lys Asp Ile Lys Lys Ile Met Glu Glu Lys Ile Gln Ile Ser
385                 390                 395                 400
Gly Ser Asn Tyr Lys Ser Leu Glu Val Leu Val Ala Asp Leu Val Asn
                405                 410                 415
Ala Gln Lys Asp Ser Met Gln Asp Glu Ser Ser Gln Thr Ser Leu Gln
            420                 425                 430
Lys Glu Ile Ser Thr Glu Glu Gln Leu Arg Arg Leu Gln Glu Glu Lys
        435                 440                 445
Leu Cys Lys Ile Cys Met Asp Arg Asn Ile Ala Ile Val Phe Val Pro
    450                 455                 460
Cys Gly His Leu Val Thr Cys Lys Gln Cys Ala Glu Ala Val Asp Lys
465                 470                 475                 480
Cys Pro Met Cys Tyr Thr Val Ile Thr Phe Lys Gln Lys Ile Phe Met
                485                 490                 495
Ser
```

<210> SEQ ID NO 9
<211> LENGTH: 411
<212> TYPE: DNA
<213> ORGANISM: artificial
<220> FEATURE:
<223> OTHER INFORMATION: synthetic construct

<400> SEQUENCE: 9

```
tctcttactc gtcgtattga tgatactatt tttcaaaatc ctatggttca agaagctatt        60
cgtatgggtt tttcttttaa agatattaaa aaaattatgg aagaaaaaat tcaaatttct       120
ggttctaatt ataaatctct tgaagttctt gttgctgatc ttgttaatgc tcaaaaagat       180
tctatgcaag atgaatcttc tcaaacttct cttcaaaaag aaatttctac tgaagaacaa       240
cttcgtcgtc ttcaagaaga aaaactttgt aaaatttgta tggatcgtaa tattgctatt       300 gttttgttc cttgtggtca tcttgttact tgtaaacaat gtgctgaagc tgttgataaa        360
tgtcctatgt gttatactgt tattactttt aaacaaaaaa ttttatgtc t                 411
```

<210> SEQ ID NO 10
<211> LENGTH: 137
<212> TYPE: PRT
<213> ORGANISM: artificial
<220> FEATURE:
<223> OTHER INFORMATION: synthetic construct

<400> SEQUENCE: 10

Ser Leu Thr Arg Arg Ile Asp Asp Thr Ile Phe Gln Asn Pro Met Val
1               5                   10                  15

Gln Glu Ala Ile Arg Met Gly Phe Ser Phe Lys Asp Ile Lys Lys Ile
            20                  25                  30

Met Glu Glu Lys Ile Gln Ile Ser Gly Ser Asn Tyr Lys Ser Leu Glu
        35                  40                  45

Val Leu Val Ala Asp Leu Val Asn Ala Gln Lys Asp Ser Met Gln Asp
    50                  55                  60

Glu Ser Ser Gln Thr Ser Leu Gln Lys Glu Ile Ser Thr Glu Glu Gln
65                  70                  75                  80

Leu Arg Arg Leu Gln Glu Glu Lys Leu Cys Lys Ile Cys Met Asp Arg
                85                  90                  95

Asn Ile Ala Ile Val Phe Val Pro Cys Gly His Leu Val Thr Cys Lys
            100                 105                 110

Gln Cys Ala Glu Ala Val Asp Lys Cys Pro Met Cys Tyr Thr Val Ile
        115                 120                 125

Thr Phe Lys Gln Lys Ile Phe Met Ser
    130                 135

<210> SEQ ID NO 11
<211> LENGTH: 1029
<212> TYPE: DNA
<213> ORGANISM: artificial
<220> FEATURE:
<223> OTHER INFORMATION: synthetic construct

<400> SEQUENCE: 11

```
atggctgaag atgctgatat gcgtaatgaa cttgaagaaa tgcaacgtcg tgctgatcaa        60
cttgctgatg aatctcttga atctactcgt cgtatgcttc aacttgttga gaatctaaaa       120
gatgctggta ttcgtactct tgttatgctt gatgaacaag tgaacaact tgatcgtgtt        180 gaagaaggta tgaatcatat taatcaagat atgaagaag ctgaaaaaaa tcttaaagat        240
```

-continued

```
cttggtaaat gttgtggtct ttttatttgt ccttgtaata aacttaaatc ttctgatgct    300
tataaaaaag cttggggtaa taatcaagat ggtgttgttg cttctcaacc tgctcgtgtt    360
gttgatgaac gtgaacaaat ggctatttct ggtggtttta ttcgtcgtgt tactaatgat    420
gctcgtgaaa atgaaatgga tgaaaatctt gaacaagttt ctggtattat tggtaatctt    480
cgtcatatgg ctcttgatat gggtaatgaa attgatactc aaaatcgtca aattaaacgt    540
attatggaaa aagctgattc taataaaact cgtattgatg aagctaatca aactgctact    600
aaaatgcttg gttctggttc tcttactcgt cgtattgatg atactatttt tcaaaatcct    660
atggttcaag aagctattcg tatgggtttt tcttttaaag atattaaaaa aattatggaa    720
gaaaaaattc aaatttctgg ttctaattat aaatctcttg aagttcttgt tgctgatctt    780
gttaatgctc aaaagattc tatgcaagat gaatcttctc aaacttctct tcaaaaagaa    840
atttctactg aagaacaact tcgtcgtctt caagaagaaa actttgtaa aatttgtatg    900 gatcgtaata ttgctattgt ttttgttcct tgtggtcatc ttgttacttg taaacaatgt    960
gctgaagctg ttgataaatg tcctatgtgt tatactgtta ttacttttaa acaaaaaatt   1020
tttatgtct                                                           1029
```

<210> SEQ ID NO 12
<211> LENGTH: 343
<212> TYPE: PRT
<213> ORGANISM: artificial sequence
<220> FEATURE:
<223> OTHER INFORMATION: synthetic construct

<400> SEQUENCE: 12

```
Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Lys Arg Ile Met Glu Lys Ala Asp Ser Asn Lys Thr Arg Ile
            180                 185                 190

Asp Glu Ala Asn Gln Thr Ala Thr Lys Met Leu Gly Ser Gly Ser Leu
        195                 200                 205

Thr Arg Arg Ile Asp Asp Thr Ile Phe Gln Asn Pro Met Val Gln Glu
    210                 215                 220
```

```
Ala Ile Arg Met Gly Phe Ser Phe Lys Asp Ile Lys Lys Ile Met Glu
225                 230                 235                 240

Glu Lys Ile Gln Ile Ser Gly Ser Asn Tyr Lys Ser Leu Glu Val Leu
            245                 250                 255

Val Ala Asp Leu Val Asn Ala Gln Lys Asp Ser Met Gln Asp Glu Ser
        260                 265                 270

Ser Gln Thr Ser Leu Gln Lys Glu Ile Ser Thr Glu Gln Leu Arg
        275                 280                 285

Arg Leu Gln Glu Glu Lys Leu Cys Lys Ile Cys Met Asp Arg Asn Ile
        290                 295                 300

Ala Ile Val Phe Val Pro Cys Gly His Leu Val Thr Cys Lys Gln Cys
305                 310                 315                 320

Ala Glu Ala Val Asp Lys Cys Pro Met Cys Tyr Thr Val Ile Thr Phe
                325                 330                 335

Lys Gln Lys Ile Phe Met Ser
            340

<210> SEQ ID NO 13
<211> LENGTH: 1029
<212> TYPE: DNA
<213> ORGANISM: artificial
<220> FEATURE:
<223> OTHER INFORMATION: synthetic construct

<400> SEQUENCE: 13
atggctgaag atgctgatat gcgtaatgaa cttgaagaaa tgcaacgtcg tgctgatcaa      60
cttgctgatg aatctcttga atctactcgt cgtatgcttc aacttgttga agaatctaaa     120
gatgctggta ttcgtactct tgttatgctt gatgaacaag gtgaacaact gaacgtatt     180
gaagaaggta tggatcaaat taataaagat atgaagaag ctgaaaaaaa tcttactgat     240
cttggtaaat tttgtggtct ttgtgtttgt ccttgtaata aacttaaatc ttctgatgct     300
tataaaaaag cttgggtaa taatcaagat ggtgttgttg cttctcaacc tgctcgtgtt     360
gttgatgaac gtgaacaaat ggctatttct ggtggtttta ttcgtcgtgt tactaatgat     420
gctcgtgaaa tgaaatgga tgaaaatctt gaacaagttt ctggtattat tggtaatctt     480
cgtcatatgg ctcttgatat gggtaatgaa attgatactc aaaatcgtca attaaacgt     540
attatgaaaa agctgattc taataaaact cgtattgatg aagctaatca aactgctact     600
aaaatgcttg ttctggttc tcttactcgt cgtattgatg atactatttt tcaaaatcct     660
atggttcaag aagctattcg tatgggtttt tcttttaaag atattaaaaa aattatggaa     720
gaaaaaattc aaatttctgg ttctaattat aaatctcttg aagttcttgt tgctgatctt     780
gttaatgctc aaaaagattc tatgcaagat gaatcttctc aaacttctct tcaaaaagaa     840
atttctactg aagaacaact tcgtcgtctt caagaagaaa actttgtaa aatttgtatg     900
gatcgtaata ttgctattgt ttttgttcct tgtggtcatc ttgttacttg taaacaatgt     960
gctgaagctg ttgataaatg tcctatgtgt tatactgtta ttacttttaa acaaaaaatt    1020
tttatgtct                                                            1029

<210> SEQ ID NO 14
<211> LENGTH: 343
<212> TYPE: PRT
<213> ORGANISM: artificial
<220> FEATURE:
<223> OTHER INFORMATION: synthetic construct

<400> SEQUENCE: 14
```

```
Met Ala Glu Asp Ala Asp Met Arg Asn Glu Leu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
        50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Lys Arg Ile Met Glu Lys Ala Asp Ser Asn Lys Thr Arg Ile
            180                 185                 190

Asp Glu Ala Asn Gln Thr Ala Thr Lys Met Leu Gly Ser Gly Ser Leu
        195                 200                 205

Thr Arg Arg Ile Asp Asp Thr Ile Phe Gln Asn Pro Met Val Gln Glu
210                 215                 220

Ala Ile Arg Met Gly Phe Ser Phe Lys Asp Ile Lys Lys Ile Met Glu
225                 230                 235                 240

Glu Lys Ile Gln Ile Ser Gly Ser Asn Tyr Lys Ser Leu Glu Val Leu
                245                 250                 255

Val Ala Asp Leu Val Asn Ala Gln Lys Asp Ser Met Gln Asp Glu Ser
            260                 265                 270

Ser Gln Thr Ser Leu Gln Lys Glu Ile Ser Thr Glu Glu Gln Leu Arg
        275                 280                 285

Arg Leu Gln Glu Glu Lys Leu Cys Lys Ile Cys Met Asp Arg Asn Ile
290                 295                 300

Ala Ile Val Phe Val Pro Cys Gly His Leu Val Thr Cys Lys Gln Cys
305                 310                 315                 320

Ala Glu Ala Val Asp Lys Cys Pro Met Cys Tyr Thr Val Ile Thr Phe
                325                 330                 335

Lys Gln Lys Ile Phe Met Ser
            340

<210> SEQ ID NO 15
<211> LENGTH: 16
<212> TYPE: PRT
<213> ORGANISM: unknown
<220> FEATURE:
<223> OTHER INFORMATION: drosophila antennapedia

<400> SEQUENCE: 15

Arg Gln Ile Lys Ile Trp Phe Gln Asn Arg Arg Met Lys Trp Lys Lys
1               5                   10                  15
```

```
<210> SEQ ID NO 16
<211> LENGTH: 11
<212> TYPE: PRT
<213> ORGANISM: Human immunodeficiency virus

<400> SEQUENCE: 16

Tyr Gly Arg Lys Lys Arg Arg Gln Arg Arg Arg
1               5                   10

<210> SEQ ID NO 17
<211> LENGTH: 16
<212> TYPE: PRT
<213> ORGANISM: artificial
<220> FEATURE:
<223> OTHER INFORMATION: synthetic construct

<400> SEQUENCE: 17

Arg Gln Ile Lys Ile Trp Phe Gln Asn Arg Arg Met Lys Trp Lys Lys
1               5                   10                  15

<210> SEQ ID NO 18
<211> LENGTH: 16
<212> TYPE: PRT
<213> ORGANISM: artificial
<220> FEATURE:
<223> OTHER INFORMATION: synthetic construct

<400> SEQUENCE: 18

Lys Lys Trp Lys Met Arg Arg Asn Gln Phe Trp Ile Lys Ile Gln Arg
1               5                   10                  15

<210> SEQ ID NO 19
<211> LENGTH: 16
<212> TYPE: PRT
<213> ORGANISM: artificial
<220> FEATURE:
<223> OTHER INFORMATION: synthetic construct

<400> SEQUENCE: 19

Arg Gln Ile Lys Ile Trp Phe Gln Asn Arg Arg Met Lys Trp Lys Lys
1               5                   10                  15

<210> SEQ ID NO 20
<211> LENGTH: 16
<212> TYPE: PRT
<213> ORGANISM: artificial
<220> FEATURE:
<223> OTHER INFORMATION: synthetic construct

<400> SEQUENCE: 20

Arg Gln Ile Lys Ile Trp Phe Pro Asn Arg Arg Met Lys Trp Lys Lys
1               5                   10                  15

<210> SEQ ID NO 21
<211> LENGTH: 16
<212> TYPE: PRT
<213> ORGANISM: artificial
<220> FEATURE:
<223> OTHER INFORMATION: synthetic construct

<400> SEQUENCE: 21

Arg Gln Pro Lys Ile Trp Phe Pro Asn Arg Arg Met Pro Trp Lys Lys
1               5                   10                  15

<210> SEQ ID NO 22
<211> LENGTH: 16
<212> TYPE: PRT
<213> ORGANISM: artificial
```

```
<220> FEATURE:
<223> OTHER INFORMATION: synthetic constrct

<400> SEQUENCE: 22

Arg Gln Ile Lys Ile Trp Phe Gln Asn Met Arg Arg Lys Trp Lys Lys
1               5                   10                  15

<210> SEQ ID NO 23
<211> LENGTH: 16
<212> TYPE: PRT
<213> ORGANISM: artificial
<220> FEATURE:
<223> OTHER INFORMATION: synthetic construct

<400> SEQUENCE: 23

Arg Gln Ile Arg Ile Trp Phe Gln Asn Arg Arg Met Arg Trp Arg Arg
1               5                   10                  15

<210> SEQ ID NO 24
<211> LENGTH: 16
<212> TYPE: PRT
<213> ORGANISM: artificial
<220> FEATURE:
<223> OTHER INFORMATION: synthetic construct

<400> SEQUENCE: 24

Arg Arg Trp Arg Arg Trp Trp Arg Arg Trp Trp Arg Arg Trp Arg Arg
1               5                   10                  15

<210> SEQ ID NO 25
<211> LENGTH: 11
<212> TYPE: PRT
<213> ORGANISM: artificial
<220> FEATURE:
<223> OTHER INFORMATION: synthetic construct

<400> SEQUENCE: 25

Tyr Gly Arg Lys Lys Arg Arg Gln Arg Arg Arg
1               5                   10

<210> SEQ ID NO 26
<211> LENGTH: 16
<212> TYPE: PRT
<213> ORGANISM: artificial
<220> FEATURE:
<223> OTHER INFORMATION: synthetic construct

<400> SEQUENCE: 26

Ala Ala Val Ala Leu Leu Pro Ala Val Leu Leu Ala Leu Leu Ala Pro
1               5                   10                  15

<210> SEQ ID NO 27
<211> LENGTH: 27
<212> TYPE: PRT
<213> ORGANISM: artificial
<220> FEATURE:
<223> OTHER INFORMATION: synthetic construct

<400> SEQUENCE: 27

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25
```